(12) United States Patent
Cacioppo et al.

(10) Patent No.: US 10,085,684 B2
(45) Date of Patent: Oct. 2, 2018

(54) STATE IDENTIFICATION IN DATA WITH A TEMPORAL DIMENSION

(71) Applicant: The University of Chicago, Chicago, IL (US)

(72) Inventors: Stephanie Cacioppo, Chicago, IL (US); John T. Cacioppo, Chicago, IL (US); Robin M. Weiss, Chicago, IL (US)

(73) Assignee: The University of Chicago, Chicago, IL (US)

( * ) Notice: Subject to any disclaimer, the term of this patent is extended or adjusted under 35 U.S.C. 154(b) by 264 days.

(21) Appl. No.: 15/066,022

(22) Filed: Mar. 10, 2016

(65) Prior Publication Data

US 2016/0262684 A1 Sep. 15, 2016

Related U.S. Application Data

(60) Provisional application No. 62/131,094, filed on Mar. 10, 2015, provisional application No. 62/213,818, filed on Sep. 3, 2015.

(51) Int. Cl.
| | |
|---|---|
| *G06F 19/00* | (2018.01) |
| *A61B 5/00* | (2006.01) |
| *A61B 5/0476* | (2006.01) |
| *G06K 9/00* | (2006.01) |
| *G16H 40/63* | (2018.01) |

(52) U.S. Cl.
CPC .......... *A61B 5/4064* (2013.01); *A61B 5/0476* (2013.01); *A61B 5/7289* (2013.01); *G06F 19/00* (2013.01); *G06K 9/00536* (2013.01); *G16H 40/63* (2018.01)

(58) Field of Classification Search
CPC ............. G06F 17/5009; G06F 11/3452; G06F 17/30598; G06F 17/18; G06F 19/3418; G06F 11/3006; G06F 17/10; G06F 17/17; G06F 17/30309; G06F 19/12; G06F 19/707; G06F 2201/84; G06F 3/013; A61B 5/7267; A61B 5/0476; A61B 5/4088; A61B 5/7253; A61B 5/02438; A61B 5/0245; A61B 5/162; A61B 5/165; A61B 5/7203; A61B 5/725; A61B 5/7264; A61B 5/7282; A61B 2017/00199; A61B 3/0025; A61B 3/113; A61B 5/0006; A61B 5/002; A61B 5/04012; A61B 5/04017; A61B 5/0402; A61B 5/04325; A61B 5/0452; A61B 5/04525; A61B 5/0468; A61B 5/1118; A61B 5/1123; A61B 5/16; A61B 5/168; A61B 5/4064; A61B 5/4076; A61B 5/6802; A61B 5/7221; A61B 5/7289; A61B 8/5207; A61B 8/5223; G06N 99/005; G06N 7/005; G06N 3/086; G06N 5/04; G06N 3/02; G06N 3/08; G06N 5/02; G06N 5/022; G06N 5/047; G06K 9/00087; G06K 9/00496; G06K 9/00523; G06K 9/00892; G06K 9/6267; G06K 9/00536; G06K 9/00617; G06K 9/6298; C12Q 2537/165; C12Q 2561/113; G06T 7/277; G06T 7/33; G06T 7/73; G06T 7/75

See application file for complete search history.

(56) References Cited

U.S. PATENT DOCUMENTS

2014/0236039 A1* 8/2014 Strokova Aksenova ....................
G06K 9/62
600/544

OTHER PUBLICATIONS

Samanta et al 2009 Proc IMechE vol. 223 Part 1 p. 1095-1109.*
Volkmer et al., Gradual Transition Detection Using Average Frame Similarity, Proceedings of the 2004 IEEE Computer Society Conference on Computer Vision and Pattern Recognition Workshops, Jun. 27, 2004.

* cited by examiner

*Primary Examiner* — Mary K Zeman
(74) *Attorney, Agent, or Firm* — Bell & Manning, LLC

(57) ABSTRACT

States are identified in a time ordered sequence of data that have a temporal component. Data that includes a plurality of snapshots is received. Each snapshot of the plurality of snapshots includes a plurality of sensor measurements captured from distinct sensors at a common time point. The plurality of snapshots are time ordered. Root mean square error (RMSE) values are computed between successive pairs of the plurality of snapshots in time order. A peak is identified in the computed RMSE values. A valley is identified in the computed RMSE values. A stable state is determined as occurring from the identified peak to the identified valley. The determined stable state is output.

20 Claims, 19 Drawing Sheets

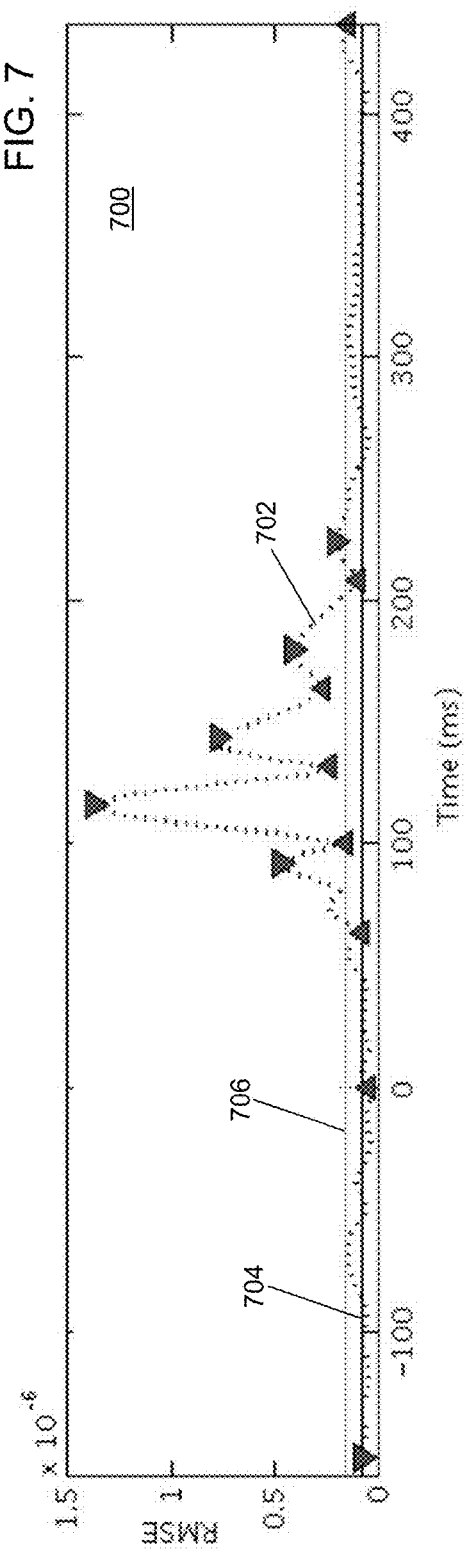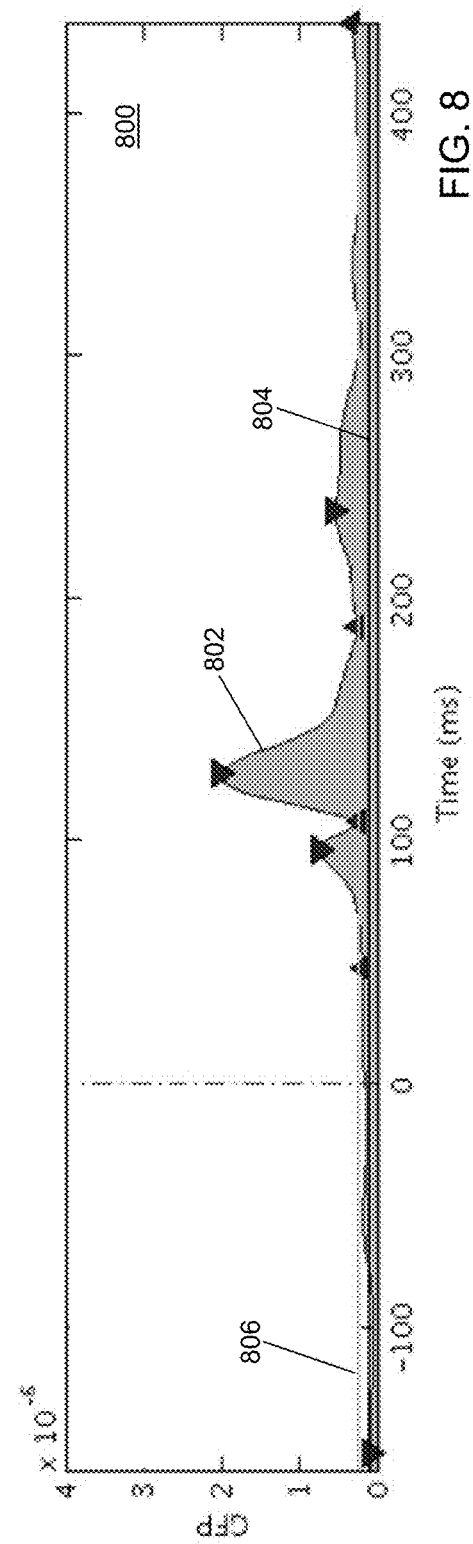

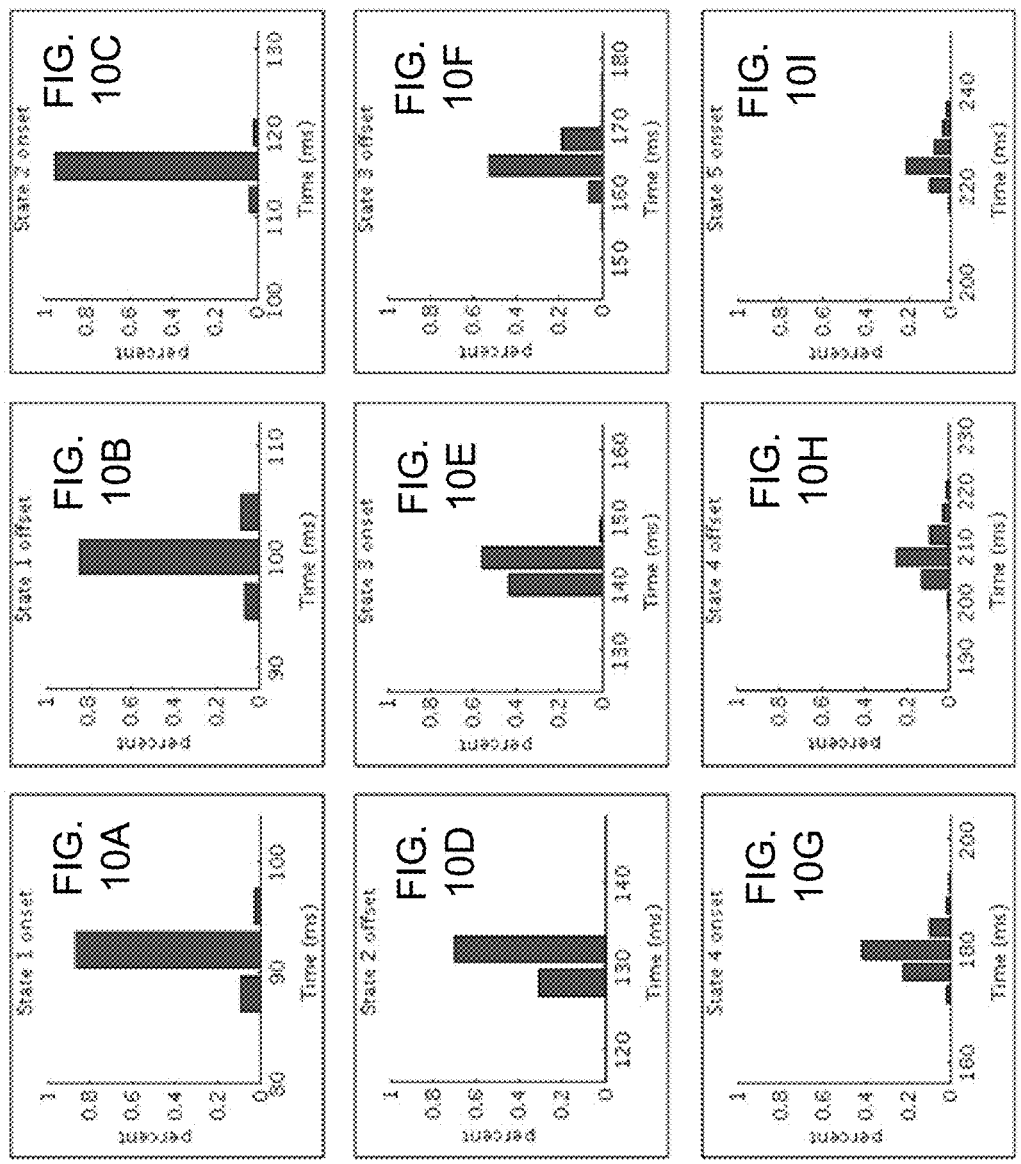

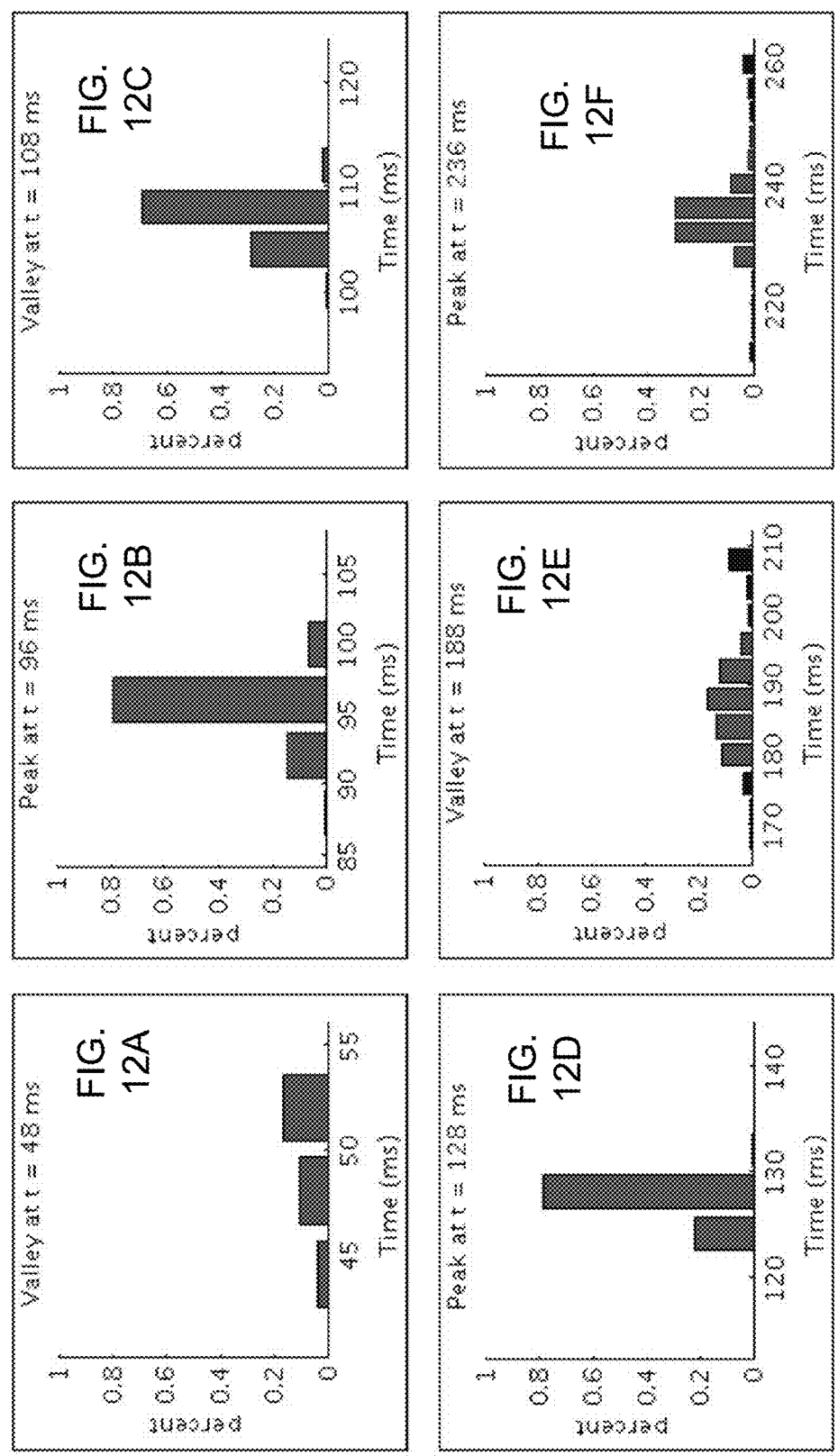

| 1300 → | Baseline | State 1 | State 2 | State 3 | State 4 | State 5 |
|---|---|---|---|---|---|---|
| Start | -152 | 92 | 116 | 144 | 180 | 224 |
| End | 0 | 100 | 132 | 164 | 208 | 436 |
| Max GFP | 0.2027 | 0.7519 | 2.0129 | 0.9554 | 0.3399 | 0.5494 |
| Avg GFP | 0.1210 | 0.7026 | 1.7615 | 0.6315 | 0.3053 | 0.3370 |
| Stddev GFP | 0.0449 | 0.0378 | 0.2732 | 0.1653 | 0.0239 | 0.1026 |

FIG. 13

| 1400 → | Valley | Peak | Valley | Peak | Valley | Peak |
|---|---|---|---|---|---|---|
| Time | 48 | 96 | 108 | 128 | 188 | 236 |
| Amplitude | 0.2001 | 0.7519 | 0.2443 | 2.0129 | 0.2719 | 0.5494 |

FIG. 14

| | Baseline | State 1 | State 2 | State 3 | State 4 | State 5 |
|---|---|---|---|---|---|---|
| Baseline | 0 | 0.9880 | 0.5226 | 0.2069 | 1.7662 | 1.1869 |
| State 1 | 0 | 0 | 1.8215 | 1.5241 | 0.8671 | 1.3141 |
| State 2 | 0 | 0 | 0 | 0.1142 | 1.6022 | 0.7410 |
| State 3 | 0 | 0 | 0 | 0 | 1.7583 | 0.9691 |
| State 4 | 0 | 0 | 0 | 0 | 0 | 1.2409 |
| State 5 | 0 | 0 | 0 | 0 | 0 | 0 |

|  | Stddev of TFs in T | Confidence Interval |
|---|---|---|
| Baseline | 0.8085 | 1.5847 |
| State 1 | 0.0055 | 0.0107 |
| State 2 | 0.0016 | 0.0030 |
| State 3 | 0.0577 | 0.1131 |
| State 4 | 0.2288 | 0.4485 |
| State 5 | 0.5130 | 1.0055 |

FIG. 16

|  | Baseline | State 1 | State 2 | State 3 | State 4 | State 5 |
|---|---|---|---|---|---|---|
| Baseline | 1 |  |  |  |  |  |
| State 1 | 1 | 1 |  |  |  |  |
| State 2 | 1 | * | 1 |  |  |  |
| State 3 | 1 | * | 1 | 1 |  |  |
| State 4 | 1 | * | * | * | 1 |  |
| State 5 | 1 | * | * | * | * | 1 |

FIG. 17

STATE IDENTIFICATION IN DATA WITH A TEMPORAL DIMENSION

CROSS-REFERENCE TO RELATED APPLICATIONS

The present application claims the benefit of 35 U.S.C. § 119(e) to U.S. Provisional Patent Application No. 62/131,094 filed on Mar. 10, 2015, and to U.S. Provisional Patent Application No. 62/213,818 filed on Sep. 3, 2015, the entire contents of which are hereby incorporated by reference.

BACKGROUND

The rapid growth of large-scale, high-spatial resolution neuroimaging technology has advanced the understanding of the neural underpinnings of various complex cognitive and social processes. For instance, work in cognitive and social neuroscience has identified the neural correlates of information processing operations, ranging from basic perceptual processing (e.g., checkerboard) to more complex cognitive (e.g., object or face recognition, decision making, action understanding, embodied cognition) and social processing (e.g., pair bonding, love, empathy, cooperation). A key theoretical objective in neuroscience and medicine is not only to specify what brain areas are recruited during a behavioral task, but also to specify when and in what specific combinations they are activated. By providing detailed information about the relationship between neuronal activity (i.e., post-synaptic dendritic potentials of a considerable number of neurons that are activated in pattern that yield a dipolar field) and the temporal resolution (millisecond by millisecond) of each component information processing operation required for behavioral performance, high-density electroencephalographic (EEG) recordings and averaged EEG (event-related potentials, ERPs) provide a tool in investigations of brain function. EEG/ERP analyses are performed in sensor space with high-density sensor recordings producing more detailed information about changes in brain activity measured across time and sensor space.

SUMMARY

In an example embodiment, a computer-readable medium is provided having stored thereon computer-readable instructions that, when executed by a computing device, cause the computing device to identify states in a time ordered sequence of data that have a temporal component. Data that includes a plurality of snapshots is received. Each snapshot of the plurality of snapshots includes a plurality of sensor measurements captured from distinct sensors at a common time point. The plurality of snapshots are time ordered and associated with a subject. Root mean square error (RMSE) values are computed between successive pairs of the plurality of snapshots in time order. A peak is identified in the computed RMSE values. A valley is identified in the computed RMSE values. A stable state is determined as occurring from the identified peak to the identified valley. The determined stable state is output for the subject.

In yet another example embodiment, a computing device is provided. The system includes, but is not limited to, a processor and a computer-readable medium operably coupled to the processor. The computer-readable medium has instructions stored thereon that, when executed by the computing device, cause the computing device to identify states in a time ordered sequence of data that have a temporal component.

In an example embodiment, a method of identifying states in a time ordered sequence of data that have a temporal component is provided.

Other principal features of the disclosed subject matter will become apparent to those skilled in the art upon review of the following drawings, the detailed description, and the appended claims.

BRIEF DESCRIPTION OF THE DRAWINGS

Illustrative embodiments of the disclosed subject matter will hereafter be described referring to the accompanying drawings, wherein like numerals denote like elements.

FIG. 7 shows the results of an RMSE analysis routine applied to the grand mean of 22 simulated individual's ERPs in accordance with an illustrative embodiment.

FIG. 8 shows the results of a GFP analysis routine applied to the grand mean of 22 simulated individual's ERPs in accordance with an illustrative embodiment.

FIGS. 10A-10I show summary statistics of the distribution of peaks/valleys found in bootstrap analysis within ±5% time windows around the locations of a peak/valley identified in the analysis of the overall RMSE in accordance with an illustrative embodiment.

FIGS. 12A-12F show summary statistics of the distribution of peaks/valleys found in bootstrap analysis within ±5% time windows around the locations of a peak/valley identified in the analysis of the overall GFP in accordance with an illustrative embodiment.

FIG. 13 shows tabular results of the RMSE and GFP computed based on the curves of FIGS. 7 and 8 in accordance with an illustrative embodiment.

FIG. 14 shows tabular results of the GFP computed based on the curves of FIG. 8 in accordance with an illustrative embodiment.

FIG. 15 shows tabular results summarizing a cosine distance between template maps for the results shown in FIGS. 7, 8, 13, and 14 in accordance with an illustrative embodiment.

FIG. 16 shows tabular results summarizing a standard deviation and a confidence interval for the cosine distance between template maps for the results shown in FIGS. 7, 8, 13, and 14 in accordance with an illustrative embodiment.

FIG. 17 shows tabular results summarizing a template map membership for the results shown in FIGS. 7, 8, 13, and 14 in accordance with an illustrative embodiment.

DETAILED DESCRIPTION

Figure 1:
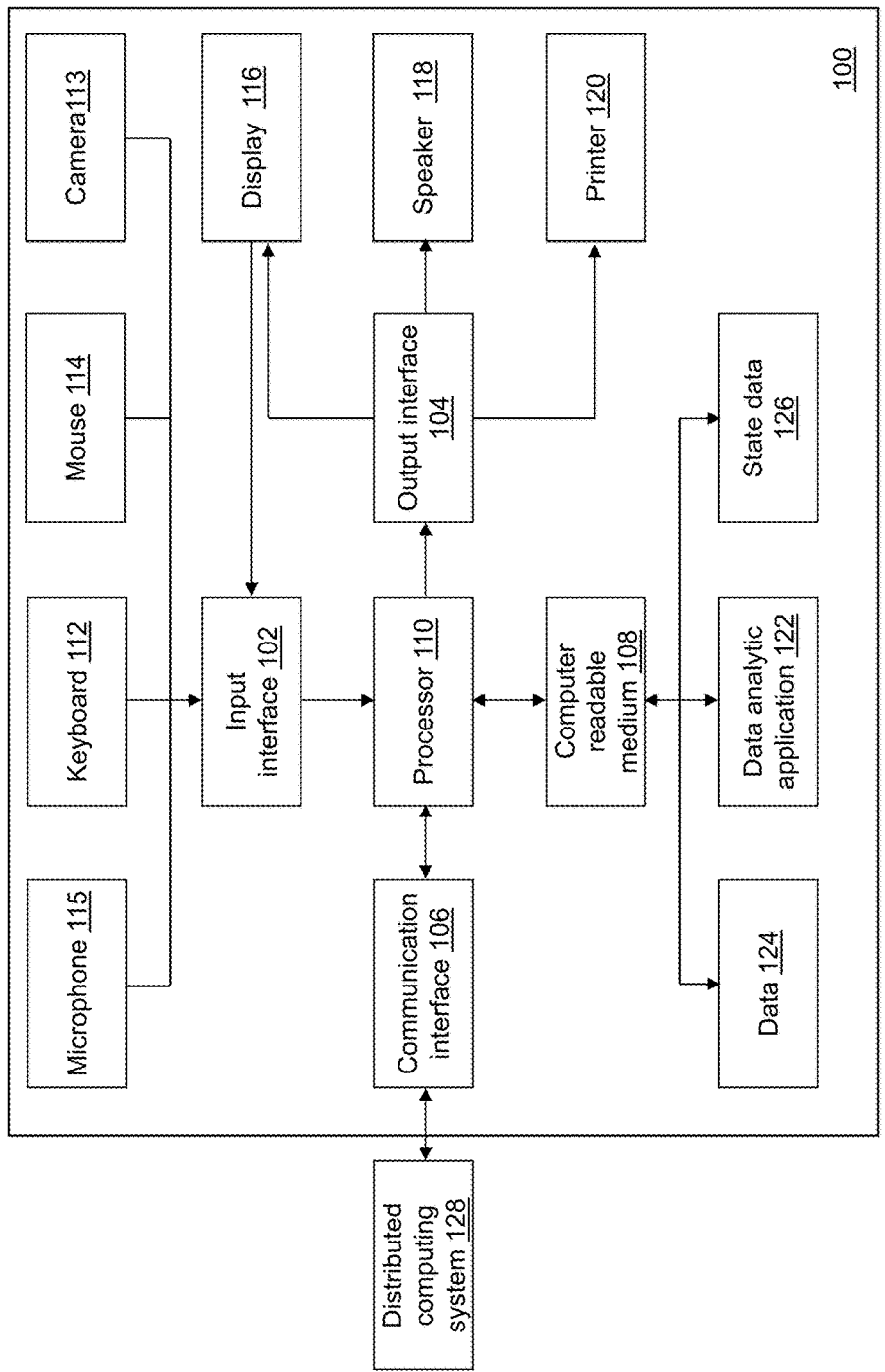
FIG. 1 depicts a block diagram of a data processing device in accordance with an illustrative embodiment.

Referring to FIG. 1, a block diagram of a data processing device 100 is shown in accordance with an illustrative embodiment. Data processing device 100 may include an input interface 102, an output interface 104, a communication interface 106, a computer-readable medium 108, a processor 110, a data analytic application 122, data 124, and state data 126. Fewer, different, and/or additional components may be incorporated into data processing device 100.

Input interface 102 provides an interface for receiving information from the user for entry into data processing device 100 as understood by those skilled in the art. Input interface 102 may interface with various input technologies including, but not limited to, a keyboard 112, a camera 113, a mouse 114, a microphone 115, a display 116, a track ball, a keypad, one or more buttons, etc. to allow the user to enter information into data processing device 100 or to make selections presented in a user interface displayed on the display. The same interface may support both input interface 102 and output interface 104. For example, display 116 comprising a touch screen provides user input and presents output to the user. Data processing device 100 may have one or more input interfaces that use the same or a different input interface technology. The input interface technology further may be accessible by data processing device 100 through communication interface 106.

Output interface 104 provides an interface for outputting information for review by a user of data processing device 100 and/or for use by another application. For example, output interface 104 may interface with various output technologies including, but not limited to, display 116, a speaker 118, a printer 120, etc. Data processing device 100 may have one or more output interfaces that use the same or a different output interface technology. The output interface technology further may be accessible by data processing device 100 through communication interface 106.

Communication interface 106 provides an interface for receiving and transmitting data between devices using various protocols, transmission technologies, and media as understood by those skilled in the art. Communication interface 106 may support communication using various transmission media that may be wired and/or wireless. Data processing device 100 may have one or more communication interfaces that use the same or a different communication interface technology. For example, data processing device 100 may support communication using an Ethernet port, a Bluetooth antenna, a telephone jack, a USB port, etc. Data and messages may be transferred between data processing device 100 and/or a distributed computing system 128 using communication interface 106.

Computer-readable medium 108 is an electronic holding place or storage for information so the information can be accessed by processor 110 as understood by those skilled in the art. Computer-readable medium 108 can include, but is not limited to, any type of random access memory (RAM), any type of read only memory (ROM), any type of flash memory, etc. such as magnetic storage devices (e.g., hard disk, floppy disk, magnetic strips, . . . ), optical disks (e.g., compact disc (CD), digital versatile disc (DVD), . . . ), smart cards, flash memory devices, etc. Data processing device 100 may have one or more computer-readable media that use the same or a different memory media technology. For example, computer-readable medium 108 may include different types of computer-readable media that may be organized hierarchically to provide efficient access to the data stored therein as understood by a person of skill in the art. As an example, a cache may be implemented in a smaller, faster memory that stores copies of data from the most frequently/recently accessed main memory locations to reduce an access latency. Data processing device 100 also may have one or more drives that support the loading of a memory media such as a CD, DVD, an external hard drive, etc. One or more external hard drives further may be connected to data processing device 100 using communication interface 106.

Processor 110 executes instructions as understood by those skilled in the art. The instructions may be carried out by a special purpose computer, logic circuits, or hardware circuits. Processor 110 may be implemented in hardware and/or firmware. Processor 110 executes an instruction, meaning it performs/controls the operations called for by that instruction. The term "execution" is the process of running an application or the carrying out of the operation called for by an instruction. The instructions may be written using one or more programming language, scripting language, assembly language, etc. Processor 110 operably couples with input interface 102, with output interface 104, with communication interface 106, and with computer-readable medium 108 to receive, to send, and to process information. Processor 110 may retrieve a set of instructions from a permanent memory device and copy the instructions in an executable form to a temporary memory device that is generally some form of RAM. Data processing device 100 may include a plurality of processors that use the same or a different processing technology.

Data analytic application 122 performs operations associated with determining state data 126 from data 124. Data 124 may include a time ordered sequence of data snapshots captured at discrete times. State data 126 may include distinct states identified in data 124. Some or all of the operations described herein may be embodied in data analytic application 122. The operations may be implemented using hardware, firmware, software, or any combination of these methods. Referring to the example embodiment of FIG. 1, data analytic application 122 is implemented in software (comprised of computer-readable and/or computer-executable instructions) stored in computer-readable medium 108 and accessible by processor 110 for execution of the instructions that embody the operations of data analytic application 122. Data analytic application 122 may be written using one or more programming languages, assembly languages, scripting languages, etc. Data analytic application 122 may be a plug-in to another application that provides additional functionality.

Data analytic application 122 may be implemented as a Web application. For example, data analytic application 122 may be configured to receive hypertext transport protocol (HTTP) responses and to send HTTP requests. The HTTP responses may include web pages such as hypertext markup language (HTML) documents and linked objects generated in response to the HTTP requests. Each web page may be identified by a uniform resource locator (URL) that includes the location or address of the computing device that contains the resource to be accessed in addition to the location of the resource on that computing device. The type of file or resource depends on the Internet application protocol such as the file transfer protocol, HTTP, H.323, etc. The file accessed may be a simple text file, an image file, an audio file, a video file, an executable, a common gateway interface application, a Java applet, an extensible markup language (XML) file, or any other type of file supported by HTTP.

Data 124 includes a plurality of time ordered sequences of data snapshots, with each time ordered sequence including a plurality of time points. A data snapshot includes, but is not limited to, data captured at an approximately common time point. A video clip may be stored in a file and define a series of data snapshots. The data stored in data 124 may include any type of content represented using any computer-readable format such as binary, alphanumeric, numeric, markup language, etc. Data 124 may be stored in computer-readable medium 108 or on computer-readable media on or accessible by one or more other computing devices, such as distributed computing system 128, and accessed using communication interface 106. Data 124 may be stored using various structures as known to those skilled in the art including a file system, a relational database, a system of tables, a structured query language database, etc. For example, data 124 may be stored in a cube distributed across a grid of computers as understood by a person of skill in the art. As another example, data 124 may be stored in a multi-node Hadoop® cluster or in a cloud of computing devices, as understood by a person of skill in the art.

Data 124 may include sensor data captured at a plurality of times with a measurement for each sensor captured at an approximately common time to create a snapshot that includes a plurality of sensor data measurements, one measurement for each sensor. Thus, a snapshot may be a vector of sensor measurements taken at an approximately common time point. Other information such as a capture time, a subject identifier, a condition identifier, etc. further may be stored in association with the snapshot. For example, the sensors may capture data for production output quality control, cell processing, medical imaging, satellite imaging, security imaging, weather formation imaging, etc. The sensors may capture measures in the form of infrared signals, radio frequency signals, thermal signals, magnetic field signals, electrical field signals, electromagnetic signals, magnetic resonance signals, optical signals, electrical current signals, electrical voltage signals, sound wave signals, etc. Data 124 further may be captured for one or more subjects (people, places, or things) and under one or more conditions.

For illustration where data 124 includes EEG/ERP data, the EEG data may be captured for a plurality of individuals who are experiencing a common plurality of different stimuli. A plurality of EEG time ordered sequences of data snapshots may be captured for each subject and condition combination for comparison. ERP data may be computed from the EEG data and may be computed for each individual, averaged across stimuli, averaged across individuals, averaged across stimuli and individuals, etc. Each individual further may be exposed to the common plurality of different stimuli a plurality of times and the ERP data averaged across the multiple exposures.

Referring to FIGS. 2A-2D and 3, example operations associated with data analytic application 122 are described. Additional, fewer, or different operations may be performed depending on the embodiment. The order of presentation of the operations of FIGS. 2A-2D and 3 is not intended to be limiting. Although some of the operational flows are presented in sequence, the various operations may be performed in various repetitions, concurrently (in parallel, for example, using threads), and/or in other orders than those that are illustrated. For example, a user may execute data analytic application 122, which causes presentation of a first user interface window, which may include a plurality of menus and selectors such as drop down menus, buttons, text boxes, hyperlinks, etc. associated with data analytic application 122 as understood by a person of skill in the art. The plurality of menus and selectors may be accessed in various orders. An indicator may indicate one or more user selections from a user interface, one or more data entries into a data field of the user interface, one or more data items read from computer-readable medium 108 or otherwise defined with one or more default values, etc. that are received as an input by data analytic application 122.

Figure 2A:
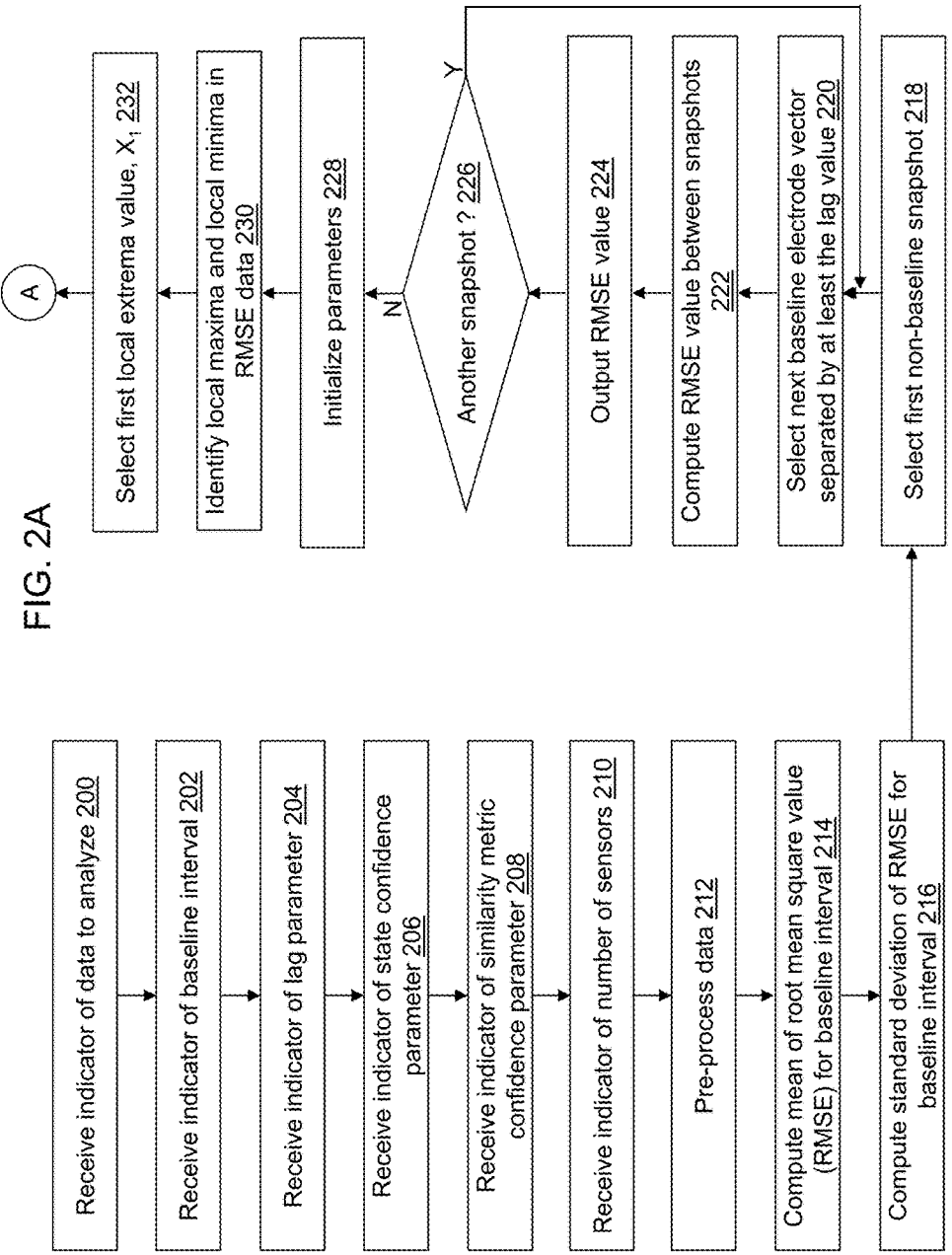
FIGS. 2A-2D and 3 depict flow diagrams of example operations performed by the data processing device of FIG. 1 in accordance with an illustrative embodiment.

Referring to FIG. 2A, in an operation 200, a first indicator is received that indicates data 124 to transform to state data 126. For example, the first indicator indicates a location of data 124. As an example, the first indicator may be received by data analytic application 122 after selection from a user interface window or after entry by a user into a user interface window. In an alternative embodiment, the data to transform may not be selectable. For example, a most recently created data set may be used automatically. The first indicator further may indicate a subset of data 124 to process. For example, the subset may be selected based on a specified time interval, based on a specified experiment, based on specified one or more subjects, based on specified one or more conditions, etc.

In an operation 202, a second indicator is received that indicates a baseline interval. The baseline interval defines a time interval within data 124 that is used to estimate noise statistics such as a mean and a standard deviation of the noise. The second indicator may indicate a start time, a stop time, and/or a duration of the baseline interval. A default value for the baseline interval may further be stored, for example, in computer-readable medium 108. Merely for illustration, a baseline interval of 400 milliseconds (ms) may be stored and used to define a duration of the baseline interval as 400 ms from a time associated with the first snapshot stored in data 124. Of course, the baseline interval may be labeled or selected in a variety of different manners by the user. The same or a different baseline interval may be defined for each subject.

In an operation 204, a third indicator is received that indicates a lag value of a lag parameter. The lag value defines a distance between snapshots that are to be compared. For illustration where data 124 includes EEG/ERP data, the lag value may be defined as a minimum duration of a putative microstate. A minimum duration of an exogenous (stimulus driven) ERP microstate may be shorter than a minimum duration of an endogenous ERP microstate. For example, a lag value of approximately 8 ms may be appropriate for basic visual tasks; whereas, a lag value of approximately 12 ms may be appropriate for a more complex cognitive task. A default value for the lag value may further be stored, for example, in computer-readable medium 108.

Of course, the lag value may be labeled or selected in a variety of different manners by the user. For illustration where data 124 includes EEG/ERP data, the lag value may be selected by identifying the complexity of the task performed while the EEG/ERP data was captured, where times associated with different complexities of tasks are stored, for example, in computer-readable medium 108.

In an operation 206, a fourth indicator is received that indicates a microstate confidence parameter value. The microstate confidence parameter value, $M_c$, may be defined based on a combination of a confidence interval and a type of statistical distribution. For illustration, when the microstate confidence parameter value is defined, the confidence interval and the distribution indicator need not be defined because the confidence interval and the distribution indicator are used to compute the microstate confidence parameter value. For illustration, a microstate confidence parameter value equal to 1.96 may be input by a user and received in operation 206, or a confidence interval equal to 95% and a distribution indicator indicating standard normal distribution may be input by a user and received in operation 206. The microstate confidence parameter value may be computed based on the confidence interval and the distribution indicator as understood by a person of skill in the art. A default value for the microstate confidence parameter value may further be stored, for example, in computer-readable medium 108. For example, a default value may be 2.575, which is associated with a 99% confidence interval and the standard normal distribution. Of course, other statistical distributions may be used.

In an operation 208, a fifth indicator is received that indicates a similarity metric confidence parameter value. The similarity metric confidence parameter value, $M_s$, may be defined based on a combination of a confidence interval and a type of statistical distribution. For illustration, when the similarity metric confidence parameter value is defined, the confidence interval and the distribution indicator need not be defined because the confidence interval and the distribution indicator are used to compute the similarity metric confidence parameter value. For example, a microstate confidence parameter value equal to 1.96 may be input by a user and received in operation 208, or a confidence interval equal to 95% and a distribution indicator indicating standard normal distribution may be input by a user and received in operation 208. The similarity metric confidence parameter value may be computed based on the confidence interval and the distribution indicator as understood by a person of skill in the art. A default value for the similarity metric confidence parameter value may further be stored, for example, in computer-readable medium 108. For example, a default value may be 2.575, which is associated with a 99% confidence interval and the standard normal distribution. Of course, other statistical distributions may be used.

Figure 18:
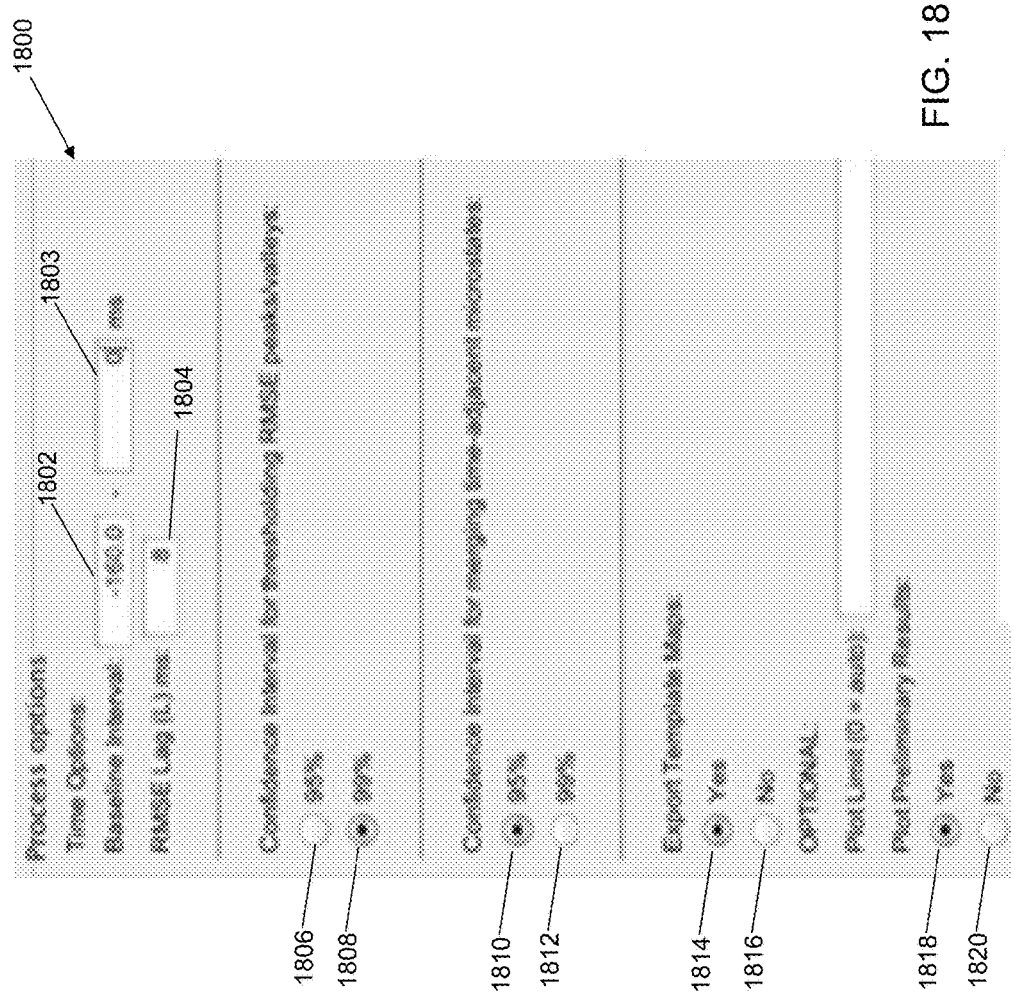
FIG. 18 shows a graphical user interface window for selecting process options in accordance with an illustrative embodiment.

For illustration, referring to FIG. 18, a user interface window 1800 provides a mechanism by which a user may define the second indicator, the third indicator, the fourth indicator, and the fifth indicator. For example, the user may enter a value for a start time of the baseline interval in a first text box 1802 and a value for an end time of the baseline interval in a second text box 1803. The user may enter the lag value of the lag parameter in a third text box 1804. The user may select the microstate confidence parameter value by selecting between a first radio button 1806 and a second radio button 1808. The user may select the similarity metric confidence parameter value by selecting between a third radio button 1810 and a fourth radio button 1812.

In an operation 210, a sixth indicator is received that indicates a number of sensors used to generate each snapshot included in data 124. A default value for the number of sensors may further be stored, for example, in computer-readable medium 108. For example, a default value may be 128. For illustration where data 124 includes EEG/ERP data, the number of sensors may be the number of electrodes used to capture the data.

In an operation 212, data 124 may be pre-processed. For illustration where data 124 includes EEG/ERP data, data 124 may be inspected for artifacts or bad channels in the recordings and EEG epochs containing eye blinks or other transient muscular and/or electric noise may be removed.

In an operation 214, a mean of a root mean square value (RMSE) may be computed for the time ordered sequence of data snapshots that occur during the baseline interval indicated in operation 202. For example, the RMSE may be computed using $$RMSE = \sqrt{\frac{\sum_{i=1}^{n}(x_i - \hat{x}_i)^2}{n}},$$

where n is the number of sensors indicated in operation 210, $x_i$ is a voltage at electrode i in a snapshot occurring at a first time during the baseline interval, and $\hat{x}_i$ is a voltage at electrode i in a snapshot occurring at a subsequent time during the baseline interval. The RMSE computed for successive pairs of snapshots during the baseline interval are averaged to compute the mean of the RMSE, $RMSE_M$. Each snapshot is a vector that includes the voltage at each electrode captured at the same time.

In an operation 216, a standard deviation of the RMSE may be computed for the time ordered sequence of data snapshots that occur during the baseline interval indicated in operation 202 by computing the square root of the sum of the square of the difference between each RMSE of a snapshot and $RMSE_M$ divided by n.

In an operation 218, a first non-baseline snapshot is selected from data 124.

In an operation 220, a next snapshot is selected from data 124. The next snapshot is separated from the first non-baseline snapshot, or previous snapshot, by at least the lag value indicated in operation 204.

In an operation 222, an RMSE value is computed between the first non-baseline snapshot, or previous snapshot, and the next snapshot using $$RMSE = \sqrt{\frac{\sum_{i=1}^{n}(x_i - \hat{x}_i)^2}{n}},$$

where n is the number of sensors indicated in operation 210, $x_i$ is a voltage at electrode i in the next snapshot, and $\hat{x}_i$ is a voltage at electrode i in the first non-baseline snapshot, or previous snapshot, when data 124 includes EEG/ERP data.

Figure 4:
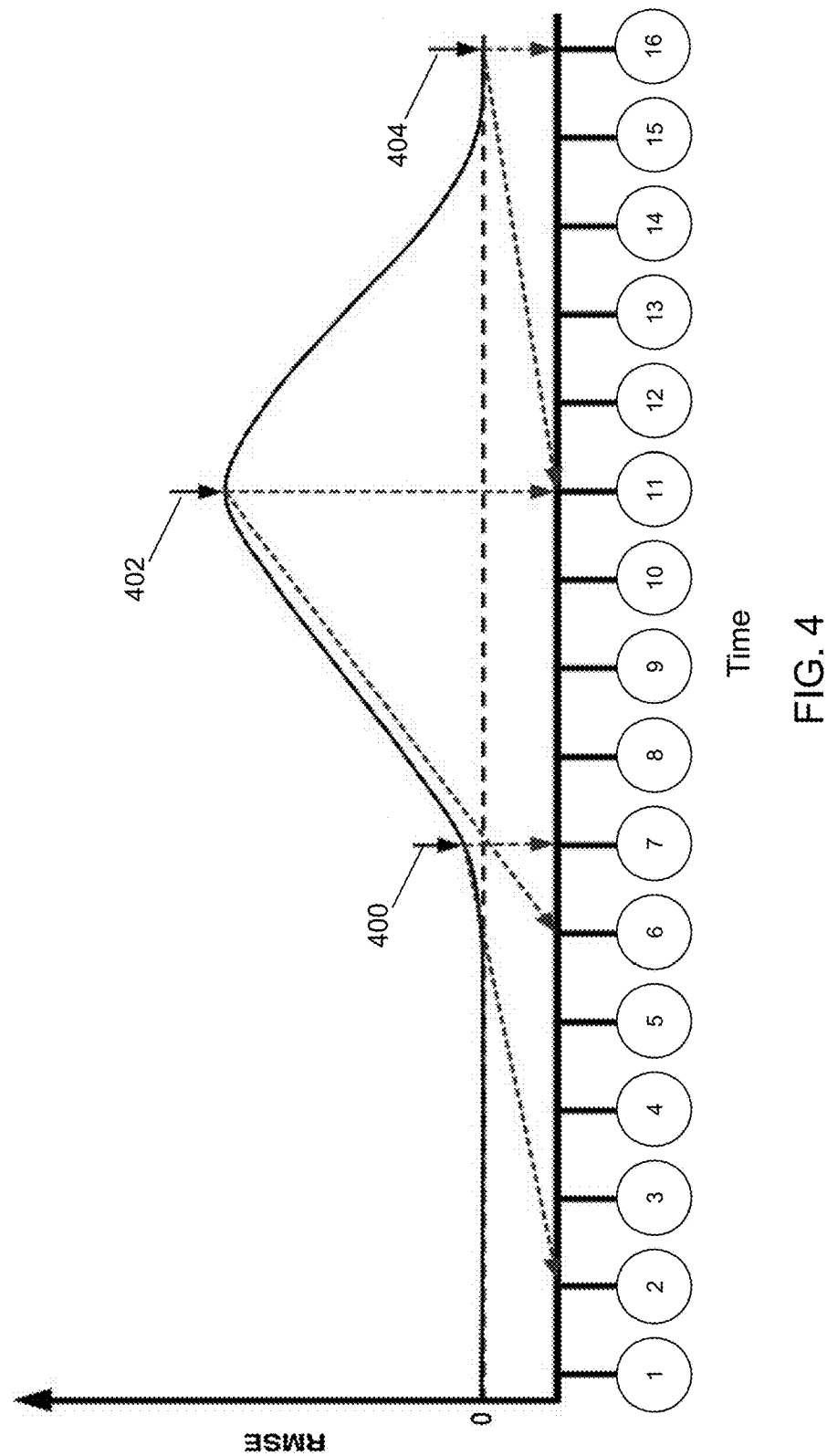
FIG. 4 illustrates an identification of stable states and a transition state in accordance with an illustrative embodiment.

In an operation 224, the computed RMSE value may be output, for example, by storing in computer-readable medium 108, by displaying in a table or graph on display 116, by printing in a table or graph by printer 120, etc. For illustration, referring to FIG. 4, values of RMSE are shown for 16 time ordered snapshots.

In an operation 226, a determination is made concerning whether or not data 124 includes another snapshot to process. If data 124 includes another snapshot to process, processing continues in operation 220 to select a next snapshot and to compute the RMSE between the newly selected next snapshot and the previously selected next snapshot, which becomes the previous snapshot. If data 124 does not include another snapshot to process, processing continues in an operation 228.

In operation 228, parameters are initialized. For example, a confidence interval parameter value, CI, may be defined as the microstate confidence parameter value, $M_c$, determined in operation 206 multiplied by the standard deviation determined in operation 216. As another example, a prior peak, $P_P$, and a prior valley, $P_T$, may be initialized to $RMSE_M$.

In an operation 230, local maxima and local minima are identified in the stored RMSE data. For example, an array may be stored in computer-readable medium 108 that includes values of local maxima and local minima, a capture time of the snapshot associated with the local maxima or local minima, and an indicator indicating whether or not the value is a local maxima or a local minima.

In an operation 232, a first local extrema, $X_1$, is selected from the identified local maxima and local minima.

Figure 2B:
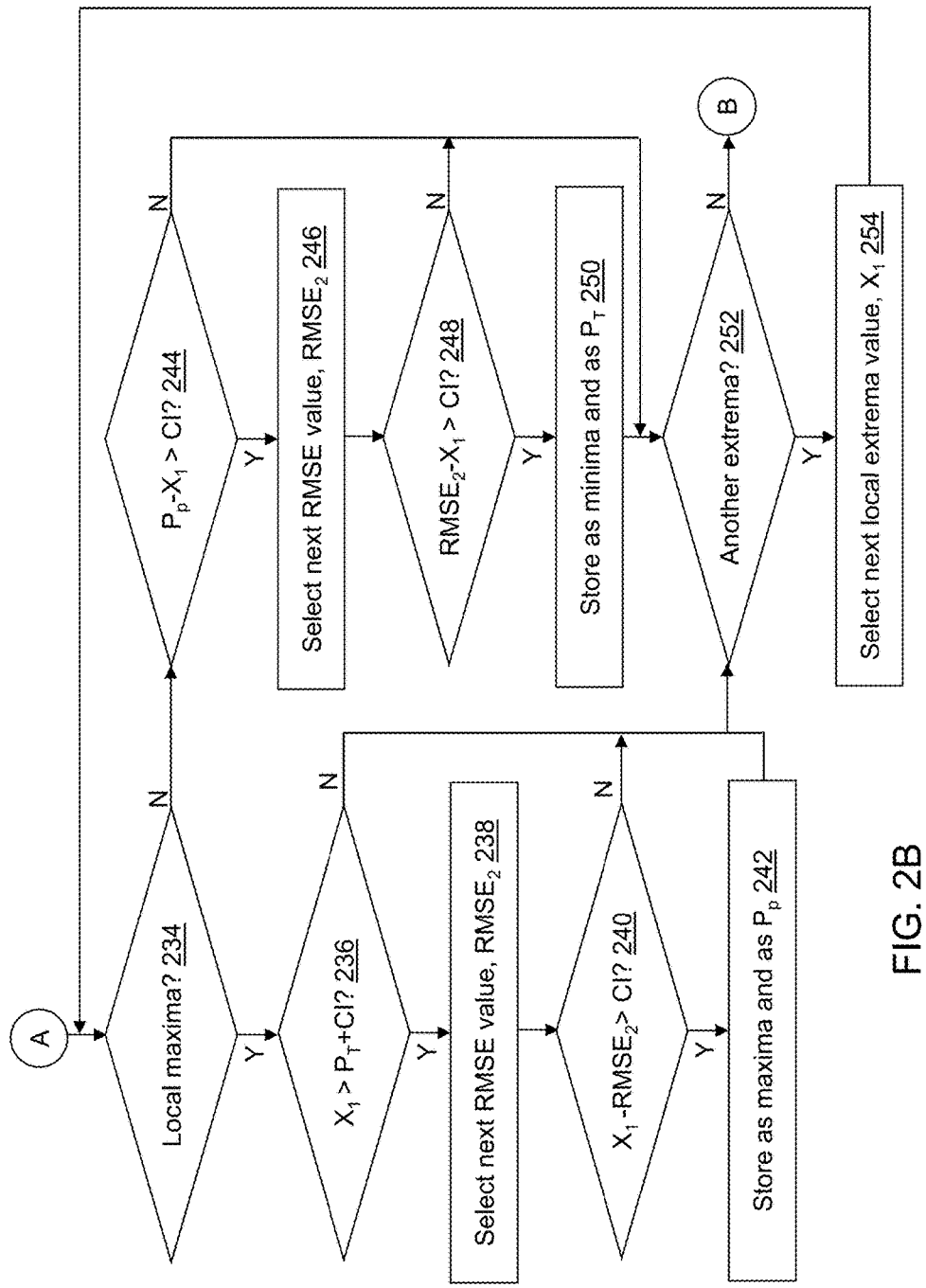

Referring to FIG. 2B, in an operation 234, a determination is made concerning whether or not first local extrema $X_1$ is a local maxima. If first local extrema $X_1$ is a local maxima, processing continues in an operation 236. If first local extrema $X_1$ is not a local maxima, processing continues in an operation 244.

In operation 236, a determination is made concerning whether or not $X_1 > P_T + CI$. If $X_1 > P_T + CI$, processing continues in an operation 238. If $X_1 \leq P_T + CI$, processing continues in an operation 252.

In operation 238, a next RMSE value, $RMSE_2$, is selected from the stored RMSE data, for example, using the capture time of the snapshot associated with the local maxima. Of course, RMSE2 may be stored in the array in association with the local maxima.

In operation 240, a determination is made concerning whether or not $X_1 - RMSE_2 > CI$. If $X_1 - RMSE_2 > CI$, processing continues in an operation 242. If $X_1 - RMSE_2 \leq CI$, processing continues in operation 252.

In operation 242, $X_1$ is stored as a maxima or peak in the RMSE data.

In operation 244, a determination is made concerning whether or not $P_p - X_1 > CI$. If $P_p - X_1 > CI$, processing continues in an operation 246. If $P_p - X_1 \leq CI$, processing continues in operation 252.

Similar to operation 238, in operation 246, a next RMSE value, $RMSE_2$, is selected from the stored RMSE data.

In operation 248, a determination is made concerning whether or not $RMSE_2 - X_1 > CI$. If $RMSE_2 - X_1 > CI$, processing continues in an operation 250. If $RMSE_2 - X_1 \leq CI$, processing continues in operation 252.

In operation 250, $X_1$ is stored as a minima or valley in the RMSE data.

In operation 252, a determination is made concerning whether or not there is another identified extrema. If there is another identified extrema, processing continues in an operation 254. If there is not another identified extrema, processing continues in an operation 256.

In operation 254, a next local extrema value is selected as $X_1$ and processing continues in operation 234.

Operations 234-254 may be used to remove local maxima/minima that represent noise in the RMSE data.

Figure 2C:
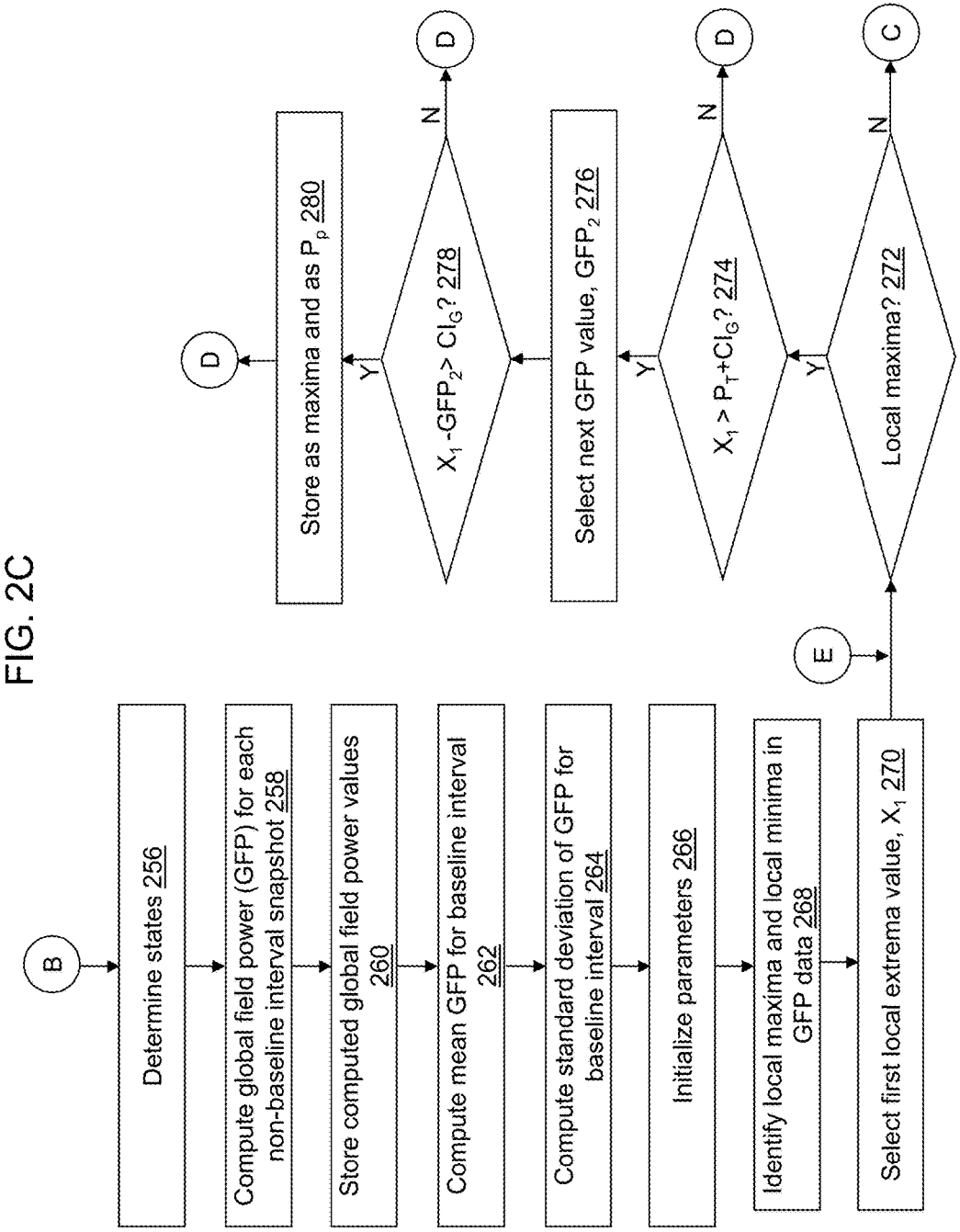

Referring to FIG. 2C, in operation 256, states are determined from the maxima and minima identified in operations 234-254. For example, a stable state may be defined as occurring from a peak (maxima) to a subsequent valley (minima), inclusive. Successive peaks to valleys are indicated as different stable states. A transition state may be defined as from the valley (minima) to the subsequent peak (maxima), exclusive. Information describing the determined states may be output, for example, by storing in computer-readable medium 108, by displaying in a table or graph on display 116, by printing in a table or graph by printer 120, etc. The state information may include a list of the snapshots included in each state based on a start time associated with the peak and a stop time associated with the subsequent valley for stable states, and based on a start time associated with the valley and a stop time associated with the subsequent peak for transition states. A state type indicator may indicate whether each state is a stable state or a transition state.

Referring again to FIG. 4, snapshots 1-6 may define a first stable state, snapshots 7-10 may define a first transition state, and snapshots 11-16 may define a second stable state with a lag value of 5 and a sampling period of 1. Point 400 reflects an onset of a transition period from a hypothetical stable state to a second state. Point 402 (a first peak) defines a start of a next state, which extends either to the end of the recording epoch or until a valley and another peak occur (not shown). The timing of each microstate is peak-to-valley, inclusive.

Referring to FIG. 7, information describing the determined states may be output in a first chart 700 that shows the RMSE as a function of time with downward arrows indicating a start time of a stable state interval and upward arrows indicating an end time of the stable state interval. First chart 700 may include an RMSE curve 702, a baseline RMSE mean curve 704, and an RMSE confidence interval curve 706. RMSE curve 702 provides the RMSE value as a function of time as computed in operation 222. Baseline RMSE mean curve 704 provides the mean RMSE value computed for the baseline interval in operation 214. RMSE confidence interval curve 706 provides the RMSE value computed for the baseline interval plus a value, such as confidence interval parameter value, CI, computed in operation 228.

Referring again to FIG. 2C, in an operation 258, a global field power may be computed for each non-baseline interval snapshot using $$GFP = \sqrt{\frac{\sum_{i=1}^{n}(x_i - \tilde{x}_i)^2}{n}},$$

where n is the number of sensors indicated in operation 210, $x_i$ is a voltage at electrode i in each non-baseline interval snapshot, and $\tilde{x}$ is an average voltage of each electrode i in the non-baseline interval snapshot when data 124 includes EEG/ERP data.

In an operation 260, the computed GFP values are stored, for example, in computer-readable medium 108.

Similar to operation 214, in an operation 262, a mean of the GFP, $GFP_M$, may be computed for the time ordered sequence of data snapshots that occur during the baseline interval indicated in operation 202.

Similar to operation 216, in an operation 264, a standard deviation of the GFP may be computed for the time ordered sequence of data snapshots that occur during the baseline interval indicated in operation 202.

Similar to operation 228, in operation 266, parameters are initialized. For example, a confidence interval parameter value, $CI_G$, may be defined as the microstate confidence parameter value determined in operation 206 multiplied by the standard deviation determined in operation 264. Of course, a different value for the microstate confidence parameter value may be used for the GFP computations in an alternative embodiment. Prior peak, $P_P$, and prior valley, $P_T$, may be initialized to $GFP_M$.

Similar to operation 230, in an operation 268, local maxima and local minima are identified in the stored GFP data.

Similar to operation 232, in an operation 270, a first local extrema, $X_1$, is selected from the identified local maxima and local minima.

Similar to operation 234, in an operation 272, a determination is made concerning whether or not first local extrema $X_1$ is a local maxima. If first local extrema $X_1$ is a local maxima, processing continues in an operation 274. If first local extrema $X_1$ is not a local maxima, processing continues in an operation 282.

Similar to operation 236, in operation 274, a determination is made concerning whether or not $X_1 > P_T + CI_G$. If $X_1 > P_T + CI_G$, processing continues in an operation 276. If $X_1 \leq P_T + CI_G$, processing continues in an operation 290.

Similar to operation 238, in operation 276, a next GFP value, $GFP_2$, is selected from the stored GFP data.

Similar to operation 240, in operation 278, a determination is made concerning whether or not $X_1 - GFP_2 > CI_G$. If $X_1 - GFP_2 > CI_G$, processing continues in an operation 280. If $X_1 - GFP_2 \leq CI_G$, processing continues in operation 290.

Similar to operation 242, in operation 280, $X_1$ is stored as a maxima or peak and processing continues in operation 290.

Figure 2D:
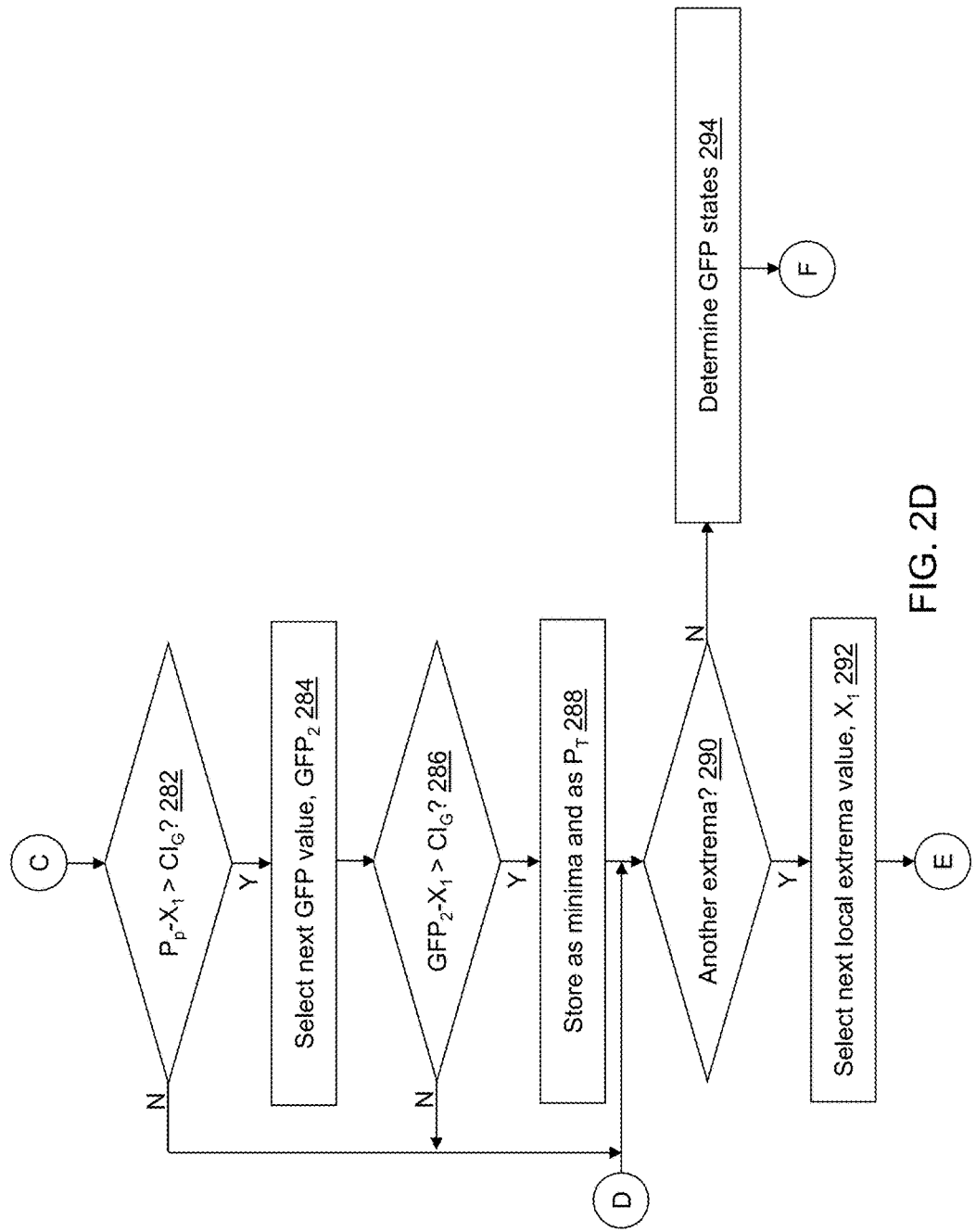

Referring to FIG. 2D, similar to operation 244, in operation 282, a determination is made concerning whether or not $P_p - X_1 > CI_G$. If $P_p - X_1 > CI_G$, processing continues in an operation 284. If $P_p - X_1 \leq CI_G$, processing continues in operation 290.

Similar to operation 238, in operation 284, a next GFP value, $GFP_2$, is selected from the stored GFP data.

Similar to operation 248, in operation 286, a determination is made concerning whether or not $GFP_2 - X_1 > CI_G$. If $GFP_2 - X_1 > CI_G$, processing continues in an operation 288. If $GFP_2 - X_1 \leq CI_G$, processing continues in operation 290.

Similar to operation 250, in operation 288, $X_1$ is stored as a minima or valley.

Similar to operation 250, in operation 290, a determination is made concerning whether or not there is another identified extrema. If there is another identified extrema, processing continues in an operation 292. If there is not another identified extrema, processing continues in an operation 294.

Similar to operation 254, in operation 292, a next local extrema value is selected as $X_1$ and processing continues in operation 272. Operations 272-292 may be used to remove local maxima/minima that represent noise.

Similar to operation 256, in operation 294, GFP states are determined from the maxima and minima identified in operations 272-292. Information describing the determined GFP states may be output, for example, by storing in computer-readable medium 108, by displaying in a table or graph on display 116, by printing in a table or graph by printer 120, etc. The information may include locations of peaks and valleys. The determined GFP states may differ in number and timing relative to the states determined in operation 256.

For illustration, referring to FIG. 8, information describing the determined GFP states may be output in a second chart 800 that shows the GFP as a function of time with downward arrows indicating a peak time and upward arrows indicating a valley time. Second chart 800 may include a GFP curve 802, a baseline GFP mean curve 804, and a GFP confidence interval curve 806. GFP curve 802 provides the GFP value as a function of time computed in operation 258. Baseline GFP mean curve 804 provides the mean GFP value computed for the baseline interval in operation 262. GFP confidence interval curve 806 provides the mean GFP value computed for the baseline interval plus a value, such as confidence interval parameter value, $CI_G$, computed in operation 266.

As another illustrative output of the determined states, referring to FIG. 13, a first table 1300 includes a start time value ("Start"), an end time value ("End"), a maximum GFP value ("Max GFP"), an average GFP value ("Avg GFP"), and a standard deviation value ("Stddev GFP") determined for the baseline and five additional states graphically depicted by RMSE curve 702 of FIG. 7. The start time values correspond with the downward arrows and the end time values correspond with the upward arrows included on RMSE curve 702 of FIG. 7. The maximum GFP value, the average GFP value, and the standard deviation value are included in first table 1300 for each state including the baseline interval.

As another illustrative output of the determined GFP states, referring to FIG. 14, a second table 1400 includes a time value ("Time") and an amplitude value ("Amplitude") determined for the GFP states graphically depicted by GFP curve 802 of FIG. 8. The valley time values correspond with the upward arrows and the peak time values correspond with the downward arrows included on GFP curve 802 of FIG. 8 excluding the start and stop times. The amplitude in the tables indicates the GFP value in microvolts (μV) determined for each valley and each peak in operation 258.

Figure 3:
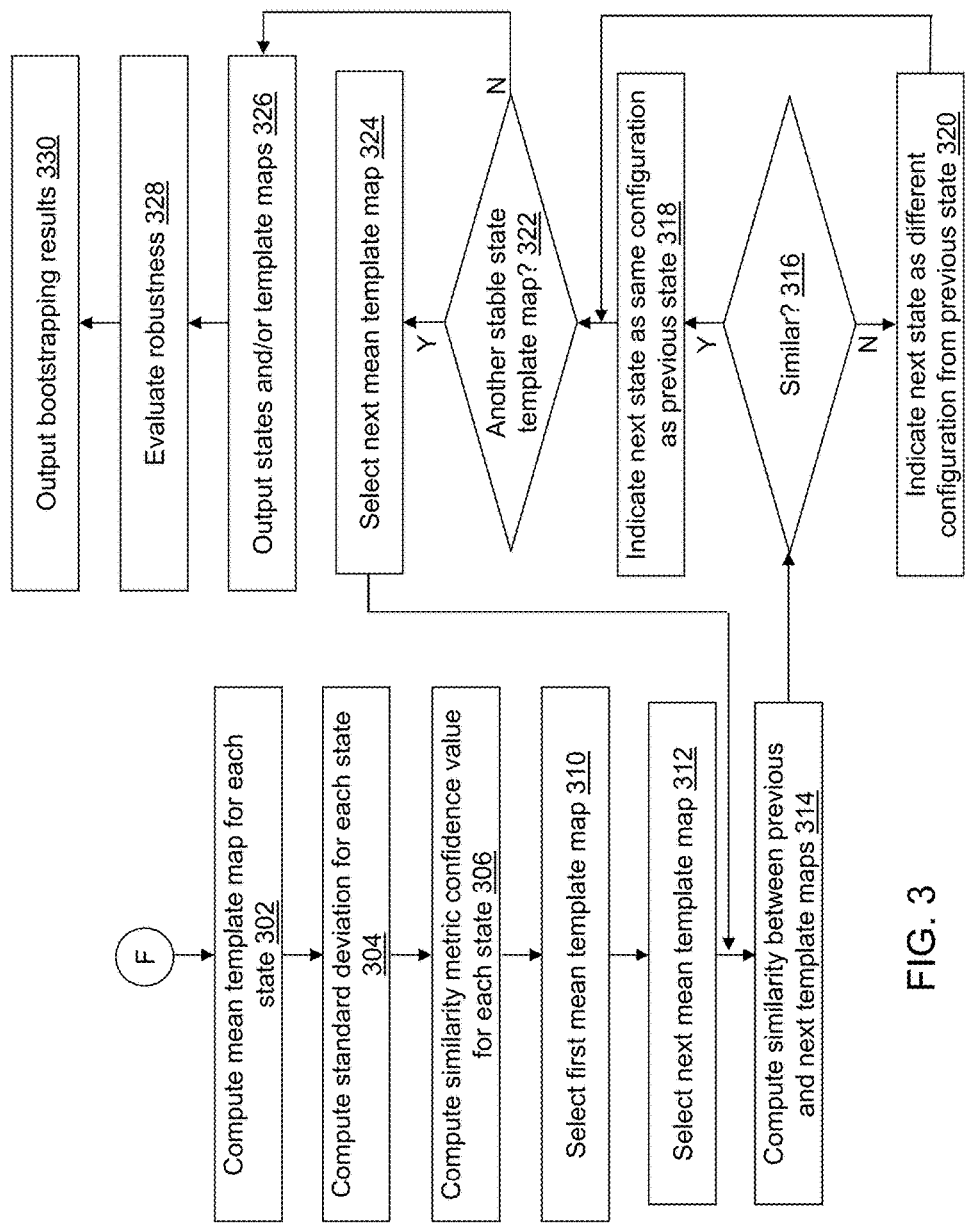

Referring to FIG. 3, in an operation 302, a mean template map is computed for each stable state determined in operations 234-254. Using the example of FIG. 4, a first mean template map is computed for the first stable state as an average of each sensor measurement of snapshots 1-6; a second mean template map is computed for the second stable state as an average of each sensor measurement of snapshots 11-16. The mean template maps may be output by storing in computer-readable medium 108, by displaying in a table or graph on display 116, by printing in a table or graph by printer 120, etc.

Figure 5:
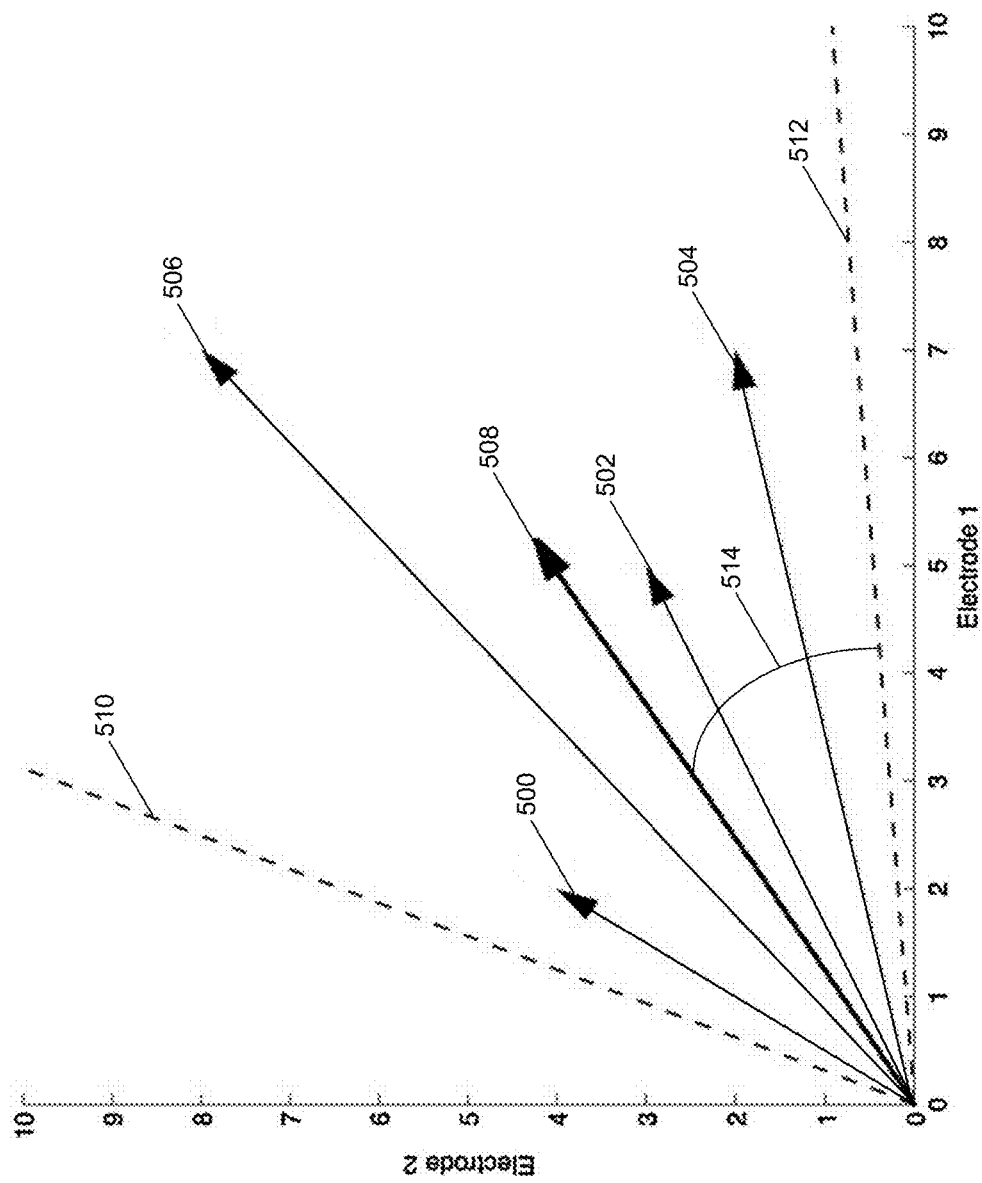
FIG. 5 illustrates a similarity evaluation relative to a mean template map in accordance with an illustrative embodiment.

For illustration, referring to FIG. 5, a snapshot includes two sensor measurements and the stable state includes a first snapshot vector 500, a second snapshot vector 502, a third snapshot vector 504, and a fourth snapshot vector 506. A mean template map vector 508 is computed as the average of the first sensor measurements and an average of the second sensor measurements.

Referring again to FIG. 3, in an operation 304, a standard deviation is computed for each state as $$SD = \sqrt{\frac{\sum_{i=1}^{m} sim(t_i, T)^2}{m}},$$

-continued $$\text{where } Sim(A, B) = 1 - \cos(\theta) = 1 - \frac{A \cdot B}{\|A\| \|B\|},$$

T is the mean template map for the stable state, m is the number of snapshots includes in the stable state, and $t_i$ is the snapshot vector.

In an operation 306, a similarity metric interval parameter value, $CI_{sm}$, may be defined as the similarity metric confidence parameter value, $M_s$, determined in operation 208 multiplied by the standard deviation determined in operation 304 for each stable state.

In an operation 310, a first mean template map is selected.

In an operation 312, a next mean template map is selected.

In an operation 314, a similarity is computed between the first mean template map and the next mean template map as $$Sim(A, B) = 1 - \cos(\theta) = 1 - \frac{A \cdot B}{\|A\| \|B\|},$$

where A is the first, or previous, mean template map vector and B is the next mean template map vector.

In an operation 316, a determination is made concerning whether or not the states have a similar configuration. If the states have a similar configuration, processing continues in an operation 318. If the states do not have a similar configuration, processing continues in an operation 320.

For example, to determine the states have a similar configuration, $Sim(A,B) < CI_{sm}$ or $Sim(A,B) \le CI_{sm}$, and to determine the states do not have a similar configuration, $Sim(A,B) \ge CI_{sm}$ or $Sim(A,B) > CI_{sm}$. For illustration, referring again to FIG. 5, this comparison has the effect of determining if B is between a maximum vector 510 and a minimum vector 512 computed relative to A or separated by an angle less than a maximum angle 514.

In operation 318, the first, or previous, mean template map vector and the next mean template map vector are indicated as having the same configuration. In operation 320, the first, or previous, mean template map vector and the next mean template map vector are indicated as having different configurations.

When data 124 includes EEG/ERP data, $CI_{sm}$ specifies a cosine distance (representing the angles around A) within which a subsequent configuration of brain activity across the n-dimensional sensor space is evaluated as equivalent or similar to the microstate (stable state) represented by A. Specifically, the next mean template map vector for the successive event-related microstate is compared to the preceding microstate, A, by calculating the cosine distance between B and A. If this value falls outside $tCI_{sm}$ around A, microstate B is interpreted, with the specified confidence, as representing a significantly different configuration of brain activity—that is, a distinct microstate whether or not GFP also changed between the two microstates. In this way, the n-dimensional cosine distance metric makes it possible to determine whether template maps for successive brain microstates differ in configuration of brain activity, GFP, or a combination of the two.

In an operation 322, a determination is made concerning whether or not there is another stable state template map. If there is another stable state template map, processing continues in an operation 324. If there is not another stable state template map, processing continues in an operation 326.

In operation 324, a next mean template map is selected. Processing continues in operation 314 with the selected next mean template map and the previously used next mean template map as the first, or previous, mean template map vector.

In operation 326, information related to the stable states, GFP states, template maps, and/or configurations is output. The information may be output, for example, by storing in computer-readable medium 108, by displaying in a table or graph on display 116, by printing in a table or graph by printer 120, etc. For illustration, referring again to FIG. 18, user interface window 1800 may also provide a mechanism by which a user may indicate whether or not the template maps are output by selecting between a fifth radio button 1814 and a sixth radio button 1816. User interface window 1800 further may provide a mechanism by which a user may indicate whether or not preliminary results are graphed by selecting between a seventh radio button 1818 and an eighth radio button 1820. The preliminary results may reference output describing changes in GFP. The preliminary results include information about microstates before they are merged using the multi-dimensional cosine similarity metric based on the cosine distance function that determines whether template maps for successive brain microstates differ in configuration of brain activity. The final results include results after the merging of the brain microstates.

For illustration, as already described the information may be presented in charts such as first chart 700 of FIG. 7, second chart 800 of FIG. 8, first table 1300 of FIG. 13, second table 1400 of FIG. 14, etc. As further illustration, FIGS. 15-17 provide quantitative information about the cosine distance between template maps, the standard deviation of cosine distances of topographic maps (i.e., the average evoked potentials at a given recording bin across n-dimensional sensor space where n the number of EEG recording channels) in each template map, and a membership identification code for the template maps, respectively. FIG. 15 shows a third table 1500 that summarizes a cosine distance between template maps for the results shown in FIGS. 7, 8, 13, and 14 in accordance with an illustrative embodiment; FIG. 16 shows a fourth table 1600 that summarizes a standard deviation and a confidence interval for the cosine distance between template maps for the results shown in FIGS. 7, 8, 13, and 14 in accordance with an illustrative embodiment; and FIG. 17 shows a fifth table 1700 that summarizes a template map membership for the results shown in FIGS. 7, 8, 13, and 14 in accordance with an illustrative embodiment.

For example, third table 1500 provides a value of the cosine metric between each unique pairs of states including the baseline interval. Fourth table 1600 provides a value of the standard deviation computed for each state in operation 304, and a value of the similarity metric interval parameter value, $CI_{sm}$, computed for each state in operation 306. Fifth table 170 provides a summary of which values did and did not fall outside $tCI_{sm}$ with the specified confidence for each unique pair of microstates. A value of "1" indicates that the pair of microstates do not represent a significantly different configuration of brain activity, and a value of "*" indicates that the pair of microstates do represent a significantly different configuration of brain activity.

In operation 328, the state determinations are evaluated for robustness. For example, when data 124 includes EEG/ERP data, the states evoked across conditions or across subjects may be evaluated for homogeneity using a bootstrapping procedure to identify heterogeneities in the timing or number of states as well as their representative template maps across analysis trials, runs, or participants. The bootstrapping procedure can be performed either within-subjects or across groups of subjects (between-subjects). In the case of within-subject bootstrapping, at each iteration a unique ERP is "bootstrapped" by a process of random selection from the available trials in a given subject's EEG recording for a given condition, with the selected trials then averaged to generate an ERP for that subject and condition. In between-subjects bootstrapping, a pre-processing step may be performed in which each subject's EEG recordings for a given condition are reduced to a within-subject ERP by averaging. The remainder of the between-subjects bootstrapping procedure is the same as the within-subjects procedure, but, instead of performing a random selection from the set of one subject's available trials, the bootstrapped ERP is generated by selecting from the set of all subjects ERPs for the given condition. In either case, a random sample of r (without replacement) of the available N possibilities is used to generate the bootstrapped ERP.

Following each bootstrap ERP generation phase, the resulting ERP (either within- or between-subjects) is subjected to the state determination described by one or more of the operations of FIGS. 2A-2D and 3. The operations may be repeated a large number of times. For example, a total number of unique bootstrapped ERPs (i.e., unique combinations of samples of size r from a population of size N) is given by (N choose r), as $$\binom{N}{r} = \frac{N!}{r!(N-r)!}.$$

For instance, if N=50 participants in a study and r=30 participants in each bootstrapped ERP, the total number of unique bootstrapped ERPs that can be calculated across these 50 participants is 50!/(30!*20!)=47,129,212,246,893. Bootstrapping can be performed on a subset of perhaps several thousand of these more than 47 trillion combinations or the entire population of bootstrapped ERPs can be generated and analyzed. The results from each run may be aggregated to determine the distribution of solutions and the robustness of the solution derived when performing the analysis on all N participants (i.e., the grand average solution). A unimodal, leptokurtic distribution of solutions for a given microstate centered on the grand average solution increases the confidence in the overall solution, whereas a multimodal, platykurtic distribution of solutions for a microstate signals that the microstate lacks robustness (e.g., significant unidentified sources of variance or moderator variables are operating). The replicability of a microstate and the performance of source localization algorithms should be superior for robust as opposed to non-robust microstates.

An empirical study of the operations of FIGS. 2A-2D and 3 was conducted using a basic visual paradigm, the reversal checkerboard task, in which a pattern reverses every 500 ms. The checkerboard task is common because there is considerable inter-subject reliability in terms of the visual ERP that it elicits. Specifically, a negative peak appears at a latency of about 70-95 ms, a larger amplitude positive peak appears at about 100-120 ms, a more variable negative peak appears around 140-160 ms, and a later, smoother positive peak around 200 ms.

Participants were 22 volunteers (8 females) with a mean age of 23.18 ($\sigma$=3.92) years. All were right-handed and had normal or corrected to-normal visual acuity. None had any prior or current neurological or psychiatric impairment as ascertained by a detailed anamnesis. The experimental design was a 2 (Task instructions: passive viewing versus active visual search)×2 (Counterbalanced Order) between-subjects factorial design. The data from the passive viewing condition was the focus because it replicates the instructional condition in the checkerboard reversal task. In this condition, participants were instructed to passively view the center of a reversing checkerboard.

The checkerboards had a spatial frequency of 1 cycle/deg, covered 5.4×5.57° of visual angle and were reversed every 500 ms. A red cross of 1° of visual angle was placed in the top center of the monitor, and the participants were instructed to fixate this cross throughout visual stimulation. Stimuli were displayed in black and white on a monitor screen, with a refresh rate of 60 hertz (Hz). Visual stimuli were presented on a computer display, which provides control of display durations and accurate recordings of reaction times. Participants were comfortably seated 100 centimeters (cm) away from the screen in which the stimuli were presented centrally. The task consisted of 250 checkerboard reversals.

Continuous surface electroencephalogram (EEG) was recorded from 128 AgAgCl carbon-fiber coated electrodes using an Electric Geodesic Sensor Net, where the EEG electrodes were arrayed in a regular distribution across the head surface and the inter-sensor distance is approximately 3 cm. The EEG was digitized at 250 Hz (corresponding to a sample period of 4 ms), with a bandwidth of 0.01-200 Hz, with the vertex electrode (Cz) serving as an on-line recording reference. Impedances were kept below 100 kilo-ohms (k$\Omega$). Data was collected in two sessions with brief intervening rest periods for the participant. The data were band pass filtered between 1 and 30 Hz with a roll-off slope of 12 decibels (dB)/Octave.

Figures 6A, 6B:
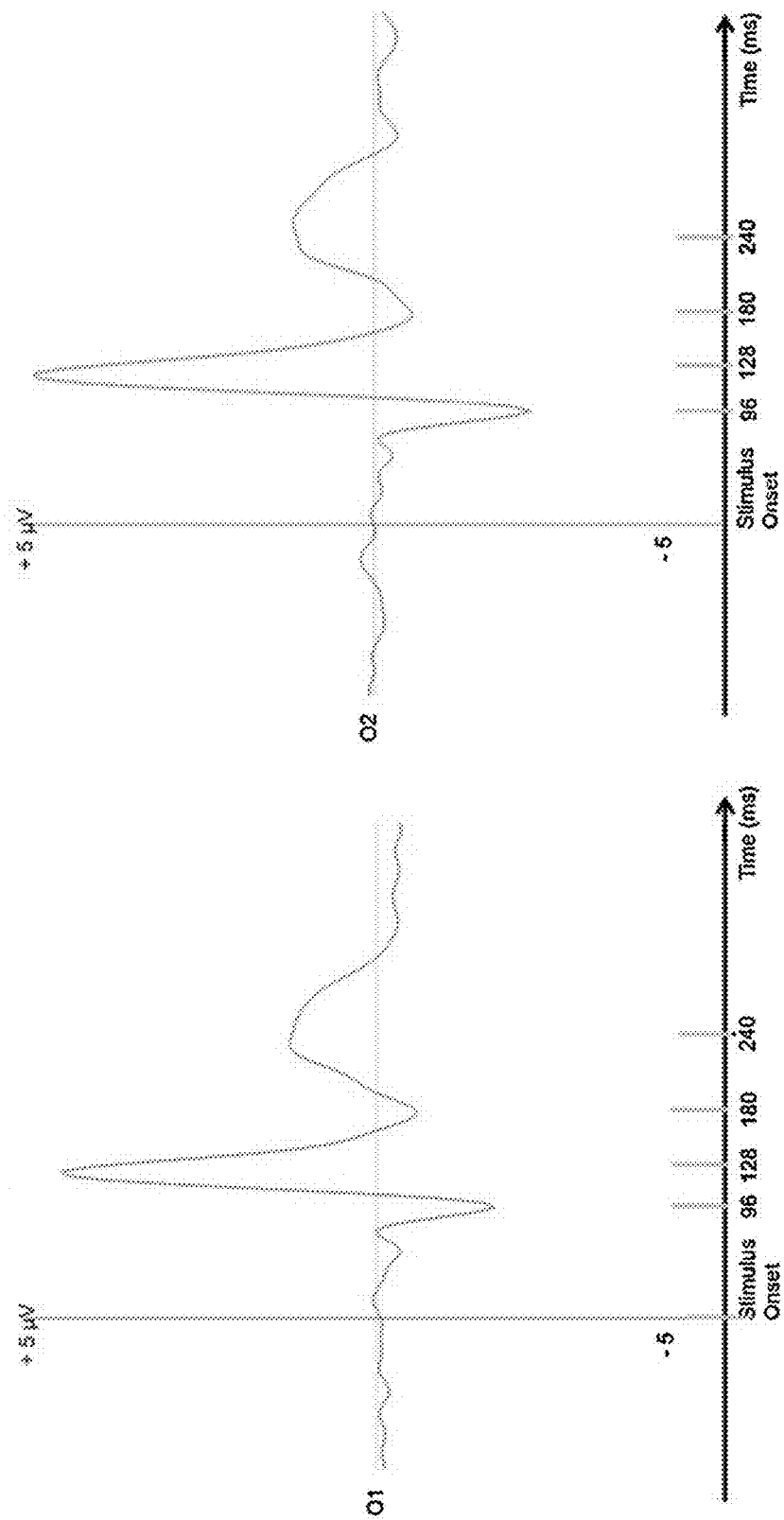
FIG. 6A shows an event-related potential (ERP) recorded over the left occipital region of the brain in accordance with an illustrative embodiment.
FIG. 6B shows an event-related potential (ERP) recorded over the right occipital region of the brain in accordance with an illustrative embodiment.

Electrophysiological data were first pre-processed at the individual level. All trials were visually inspected for oculo-motor (saccades and blinks), muscles, and other artifacts. Channels with corrupted signals were interpolated. Surviving epochs of EEG were averaged for each participant to calculate the ERP. The ERP is illustrated in FIG. 6A for the O1 recording sites and in FIG. 6B for the O2 recording sites. The ERP morphology observed over the O1 and O2 sensor sites was similar to that observed previously, with a negative peak around 96 ms, a larger positive peak around 128 ms, a second negative peak around 180 ms, and a smoother positive peak around 240 ms.

The RMSE and the GFP segmentation algorithms of FIGS. 2A-2D and 3 were applied to the high-density ERP grand average recorded across the scalp. The lag value was specified as 8 ms, a 99% confidence interval for the microstate confidence parameter value was used to construct thresholds for the RMSE and GFP analyses, and a 95% confidence interval for the similarity metric confidence parameter value was used for the similarity metric analyses. FIG. 7 shows the RMSE as a function of time. The RMSE results identified: (a) a stable baseline configuration from the start of the baseline (−152 ms) to stimulus onset at 0 ms, (b) a first stable state from 92-100 ms, (c) a second stable state from 116-132 ms, (d) a third stable state from 144-164 ms, (e) a fourth stable state from 180-208 ms, and (f) a fifth stable state from 224-436 ms as summarized in first table 1300 of FIG. 13.

FIG. 8 shows the GFP as a function of time. The GFP results identified a first valley at 48 ms, a first peak at 96 ms, a second valley at 108 ms, a second peak at 128 ms, a third valley at 188 ms, and a third peak at 236 ms as summarized in second table 1400 of FIG. 14.

A 128-dimensional similarity metric analysis was performed next to determine whether each successive state represented a significant change from the preceding state in the overall configuration of electrical activity across the sensor space. The cosine distance between each contiguous pair of states fell outside the 95% confidence interval for the earlier of the two stable states, indicating five distinct stable states as summarized in third table 1500 of FIG. 15. Specifically, the cosine distance between stable state 1 and stable state 2 was 1.82, which fell well outside the 95% confidence interval for stable state 1 of 0.011. Similarly, the 95% confidence interval and cosine distance between each of the succeeding stable states was (i.e., stable states 2 and 3, stable states 3 and 4, stable states 4 and 5) fell outside the 95% confidence interval of the earlier of the two stable states (Sim(A,B)=0.114, 1.76, and 1.24, respectively; $CI_{sm}$=0.003, 0.113, and 0.449, respectively).

Figure 9A:
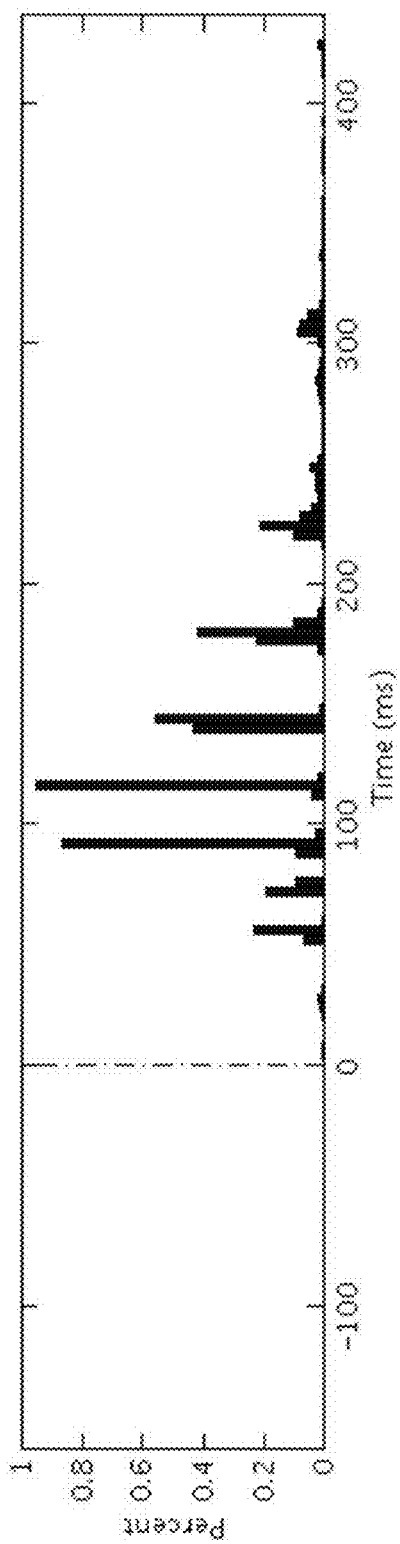
FIG. 9A shows a summary of the results of 1000 bootstrap RMSE analyses to identify locations of peaks in accordance with an illustrative embodiment.
Figure 9B:
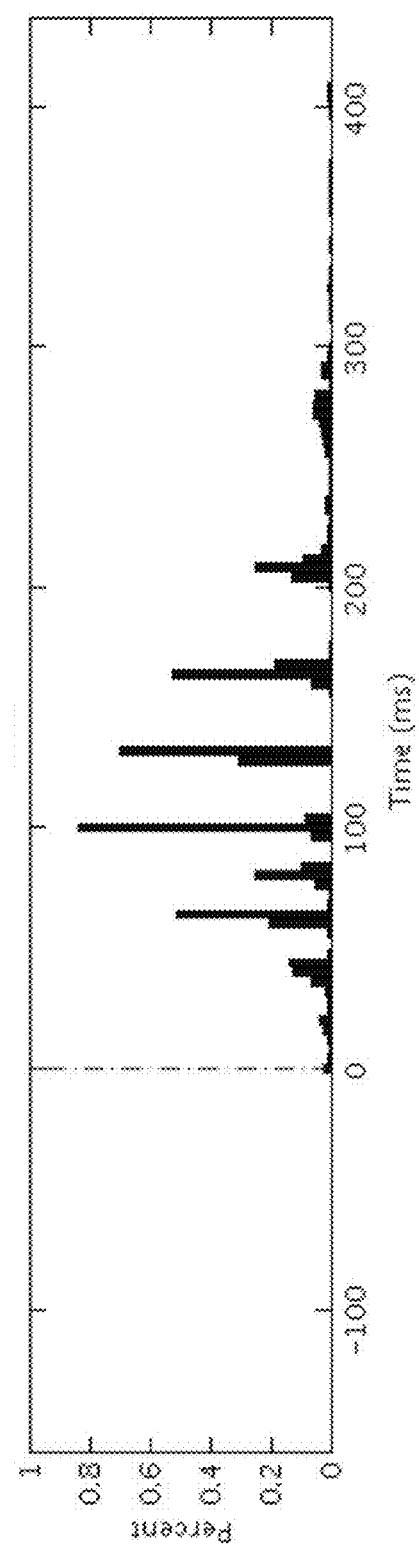
FIG. 9B shows a summary of the results of 1000 bootstrap RMSE analyses to identify locations of valleys in accordance with an illustrative embodiment.

FIG. 9A shows the between-subjects bootstrapping results for the RMSE peak analysis with 1000 bootstrap RMSE analyses to identify the onsets and offsets of the states. FIG. 9B shows the between-subjects bootstrapping results for the RMSE valley analysis with 1000 bootstrap RMSE analyses to identify the onsets and offsets of the states. In each application of the bootstrap routine, 11 out of the available 22 individual ERPs were selected at random, averaged together, and the resulting ERP subjected to the RMSE state identification operations 214-256 of FIGS. 2A to 2C. Temporal locations of peaks/valleys were accumulated over the 1000 iterations and normalized by the number of iterations to compute the percentage of bootstrap runs in which a peak/valley is identified at a specific sampling bin.

FIGS. 10A-10I show a summary of the distribution of a time of occurrence of peaks/valleys found in bootstrap analysis within ±5% time windows around the stable state onset (or offset) identified in the analysis of the overall RMSE curve. FIG. 10A shows an onset of stable state 1 at t=92 ms. The time-weighted mean of peaks in the ±5% windows is 91.74 ms. Bootstrap results indicate a peak in 97.9% of the runs within the ±5% time windows.

FIG. 10B shows an offset of stable state 1 at t=100 ms. The time-weighted mean of valleys in the ±5% windows is 100.08 ms. Bootstrap results indicate a valley in 98.3% of the runs within the ±5% time windows.

FIG. 10C shows an onset of stable state 2 at t=116 ms. The time-weighted mean of peaks in the ±5% windows is 115.9 ms. Bootstrap results indicate a peak in 100% of the runs within the ±5% time windows.

FIG. 10D shows an offset of stable state 2 at t=132 ms. The time-weighted mean of valleys in both the ±5% and ±10% windows is 130.8 ms. Bootstrap results indicate a valley in 100% of the runs within the ±5% time windows.

FIG. 10E shows an onset of stable state 3 at t=144 ms. The time-weighted mean of peaks in the ±5% windows is 142.3 ms. Bootstrap results indicate a peak in 99.9% of the runs within the ±5% time windows.

FIG. 10F shows an offset of stable state 3 at t=164 ms. The time-weighted mean of valleys is 164.62 ms in the ±5% windows. Bootstrap results indicate a valley in 77.6% of the runs within the ±5% time windows.

FIG. 10G shows an onset of stable state 4 at t=180 ms. The time-weighted mean of peaks is 179.34 ms in the ±5% windows. Bootstrap results indicate a peak in 77.4% of the runs within the ±5% time windows.

FIG. 10H shows an offset of stable state 4 at t=208 ms. The time-weighted mean of valleys is 208.23 ms in the ±5% windows. Bootstrap results indicate a valley in 50.8% of the runs within the ±5% time windows.

FIG. 10I shows an onset of stable state 5 at t=224 ms. The time-weighted mean of valleys is 225.0 ms in the ±5% windows. Bootstrap results indicate a peak in 44.4% of the runs within the ±5% time windows. The end of the recording interval was uniformly identified as the offset of stable state 5.

The results indicated more robust state identification for early than late stable states, as would be expected. Specifically, in the first 2 stable states the bootstrapping indicated 98-100% homogeneity; whereas, in the last 2 stable states, the bootstrapping indicated homogeneity had dropped to 50-60%. The bootstrapping also indicated that five stable states were identified in only 26.8% of the runs. Although this was the modal solution, four stable states were identified in 20.3% of the runs, six stable states were identified in 23.1% of the runs, and seven stable states were identified in 14.4% of the runs. The remaining 15.4% of the runs identified various numbers of stable states ranging from two to ten. Together, these results suggest that all participants may not be showing the same stable state structure during the reverse checkerboard task, and specifically that any such individual differences in the neural responses to this task are especially likely to be emerging after the second stable state (i.e., after 132 ms).

Inspection of the GFP function shown in FIG. 8 indicates three distinct epochs during which time the GFP changed. The GFP increased from basal levels beginning at 48 ms post-stimulus, peaking at 96 ms, falling to a valley at 108 ms, increasing to a second peak at 128 ms, falling to a valley at 188 ms, rising to a third (but lower) peak at 236 ms where it remained fairly stable through the rest of the recording period as summarized in second table 1400.

Figure 11A:
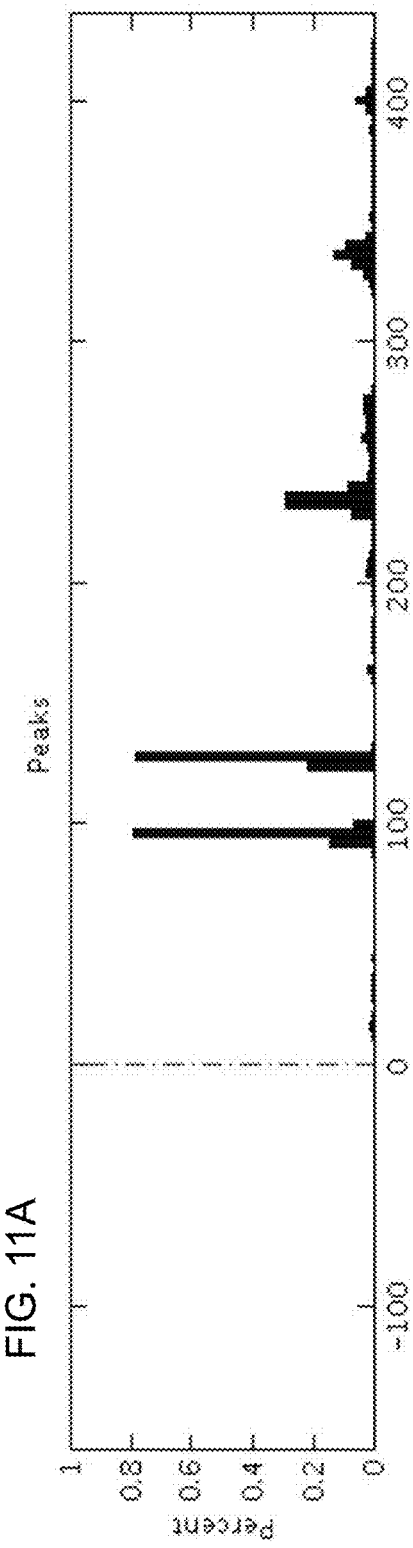
FIG. 11A shows a summary of the results of 1000 bootstrap GFP analyses to identify locations of peaks in accordance with an illustrative embodiment.
Figure 11B:
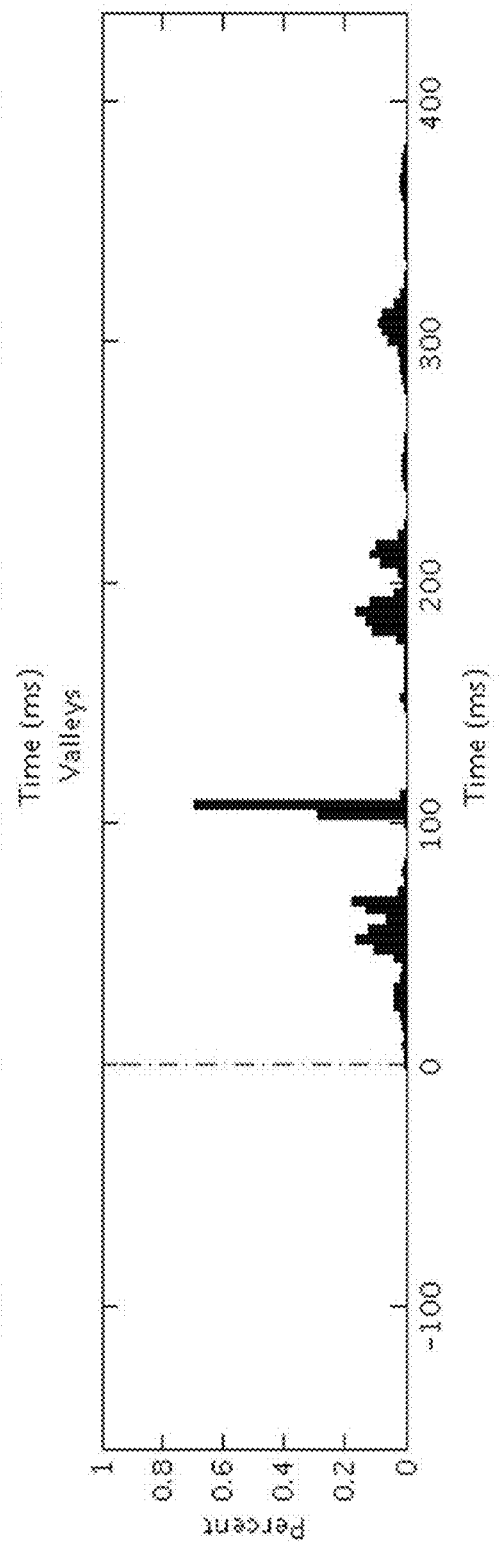
FIG. 11B shows a summary of the results of 1000 bootstrap GFP analyses to identify locations of valleys in accordance with an illustrative embodiment.

Between-subjects bootstrapping was performed to investigate how robust these changes in GFP were across subjects. The GFP analysis was performed on the same bootstrapped ERPs used in the RMSE analyses. The results are presented in FIG. 11A for the peaks and in FIG. 11B for the valleys.

Summary statistics of the distribution of peaks/valleys found in bootstrap analysis within ±5% time windows around the locations of a peak/valley identified in the analysis of the overall GFP curve are presented in FIGS. 12A-12F. FIG. 12A shows the GFP valley at t=48 ms. The time-weighted mean of valleys in the ±5% windows was 49.67 ms. Bootstrap results indicate a valley in 30.1% of the runs within the ±5% time windows.

FIG. 12B shows the GFP peak at t=96 ms. The time-weighted mean of peaks in the ±5% time windows was 95.69 ms. Bootstrap results indicate a peak in GFP in 99.7% of the runs within the ±5% windows.

FIG. 12C shows the GFP valley at t=108 ms. The time-weighted mean of valleys in the ±5% time windows was 106.93 ms. Bootstrap results indicate a valley in GFP in 99.7% of the runs within the ±5% windows.

FIG. 12D shows the GFP peak at t=128 ms. The time-weighted mean of peaks in the ±5% windows was 127.14 ms. Bootstrap results indicate a peak in 100% of the runs within the ±5% windows.

FIG. 12E shows the GFP valley at t=188 ms. The time-weighted mean of valleys in the ±5% time windows was 186.87 ms. Bootstrap results indicate a valley in GFP in 54.9% of the runs within the ±5% windows.

FIG. 12F shows the GFP peak at t=236 ms. The time-weighted mean of peaks in the ±5% time windows was 235.9 ms. Bootstrap results indicate a peak in GFP in 76.5% of the runs within the ±5% windows. The results paralleled those for RMSE, with the overall analysis showing reasonably robust results with increasing variability during the latter segments of the post-stimulus period.

When data 124 includes EEG/ERP data, microstates are conceptualized as a time-limited information processing operation in the brain. The determined states identify quasi-stable, non-periodic, event-related microstates of the brain based on changes in the pattern of global electrical activity as measured by high-density EEG. An RMSE metric is applied to high-density ERP data to identify the transition states across discrete event-related brain states, and the GFP time series is analyzed to identify changes in the overall level of activation of the brain. To determine whether the microstates identified by the RMSE metric differ in the configuration of brain activity, the GFP, or a combination of the two, an n-dimensional cosine distance similarity metric may be used to determine whether the template map for a putative microstate differs from the template map from the preceding microstate as described previously with reference to operations 302-324 of FIG. 3. A bootstrapping procedure may be used to assess the extent to which the determined states are robust (reliable, generalizable).

Similar to operation 326, in an operation 330, information related to the stable states, GFP states, template maps, and/or configurations of the bootstrapping results may be output. Example output bootstrapping results data includes the results presented in FIGS. 9A, 9B, 10A-10I, 11A, 11B, and 12A-12I. The information may be output, for example, by storing in computer-readable medium 108, by displaying in a table or graph on display 116, by printing in a table or graph by printer 120, etc.

The transition between microstates need not be all or none, but rather may be incremental. For this reason, the micro-segmentation improves the specification of the configuration, number, timing, and duration of event-related microstates by distinguishing among microstates, transition states, and changes in GFP. The resulting parameters each reflect unique information about brain function, and each can be subjected to statistical analysis to determine the effects of various within-subjects and between-subjects factors to investigate information processing in the normal, waking human brain. Moreover, hypothesis testing is improved by eliminating confirmatory bias that results from an investigator specifying a priori how many event-related microstates should be observed, and by increasing the ways in which empirical evidence can disconfirm an investigator's a priori hypotheses, improve replicability, and promote empirically grounded hypothesis generation.

The results of the simulation studies confirmed that the micro-segmentation process correctly identified stable periods and changes in the overall pattern of brain activity independent of GFP. For example, if the location of activation across the scalp changed, but the overall activity did not change, the micro-segmentation process correctly identified this as a new microstate. On the other hand, if the location of activation did not change, but the overall activity did, the micro-segmentation process correctly identified this as a change in activity (power), but not a change in microstate.

The transition states may be of considerable interest as they putatively represent the transfer of information between microstates. The transition states, therefore, may provide information about the nature and timing of this information transfer through the brain. Second, information extracted early in the processing of a stimulus is consistent with a range of possible responses, and each of these responses receives initial activation. As information continues to accumulate, activation continues to accumulate in response channels that remain viable. A given response is evoked when the activation of its channel exceeds a criterion. Importantly, continuous flow models of information processing reject the notion that information proceeds in a step-by-step fashion in which the computations performed at any given step (or microstate) are completed before any information is passed onto the next step (or microstate). Instead, information processing is depicted as proceeding through a series of computations in a semi-continuous fashion. It is conceivable that the transition states provide a means of investigating the effects of experimental conditions on this information flow.

Users can use data analytic application 122 to form, test, and interpret a priori statistical contrasts between experimental conditions based on orthogonal contrasts comparing pairs of event-related ERP waveforms. For a factor with two levels, this is simply a contrast between the ERP waveforms between the two levels; for a factor with three levels, this means specifying a priori two orthogonal contrasts (e.g., level 1 vs. level 2; level 3 vs. mean of level 1 & level 2; etc.).

Considering a two-factor mixed model with A (a1, a2)×B (b1, b2), in which A serves as a between-subject factor and B serves as a within-subject factor, procedures for a one-factor between-subjects design for a main effect for Factor A involves the following steps though the steps need not be performed sequentially unless a specific order is indicated based on a need for a previous computation:

(1) Average a1b1 snapshots (i.e., n-dimensional ERP waveform) and a1b2 snapshots to create a snapshot for Mn_a1.
(2) Average the a2b1 and a2b2 snapshots to create a snapshot for Mn_a2.
(3) Compute a difference snapshot between the Mn_a1 and Mn_a2 snapshots to create a snapshot Dmn for the Main Effect for A.
(4) Average the Mn_a1 and Mn_a2 snapshots to create a snapshot Gmn for a Grand Mean.
(5) Determine the stable and transition states for Mn_a1.
(6) Determine the stable and transition states for Mn_a2.
(7) Determine the stable and transition states for Gmn to determine the periods of time in which the brain states did not differ as a function of Factor A.
(8) Determine the stable and transition states for Dmn to identify the periods of time in which the ERP waveform did and did not differ significantly as a function of Factor A.
(9) For the time period(s) identified in Step 8 that show no significant differences in ERP waveform as a function of Factor A, refer to the results from Step 7 to characterize the evoked brain microstates across Factor A. That is, for the time period(s) that the ERP waveform did not differ as a function of Factor A, identify the microstate structure based on the results of Step 7 (i.e., Grand Mean, Gmn) and perform brain source localization on each of these microstate(s).
(10) For the time period(s) identified in Step 8 that show significant differences in ERP waveform as a function of Factor A, refer to the results from Step 5 and Step 6 to characterize the distinct evoked brain microstates within each level of Factor A. That is, for the time period(s) that the ERP waveform did differ as a function of Factor A, identify the microstate structure separately for each level of Factor A (i.e., Step 5 and Step 6 above) and perform brain source localization on each of these microstate(s).

Procedures for a one-factor within-subjects design for a main effect for Factor B may involve the following steps though the steps need not be performed sequentially unless a specific order is indicated based on a need for previous computations:

(1) Average the a1b1 snapshots (i.e., n-dimensional ERP waveform) and a2b1 snapshots to create a snapshot for Mn_b1.
(2) Average the a1b2 and a2b2 snapshots to create a snapshot for Mn_b2.
(3) Compute a difference snapshot between the Mn_b1 and Mn_b2 snapshots to create a snapshot DmnB for the Main Effect for B.
(4) Average the Mn_b1 and Mn_b2 snapshots to create a snapshot GmnB for a Grand Mean.
(5) Determine the stable and transition states for Mn_b1.
(6) Determine the stable and transition states for Mn_b2.
(7) Determine the stable and transition states for GmnB to identify the periods of time in which the brain microstates did not differ as a function of Factor B.
(8) Determine the stable and transition states for DmnB to identify the periods of time in which the ERP waveform did and did not differ significantly as a function of Factor B.
(9) For the time period(s) in which Step 8 shows no significant differences in ERP waveform as a function of Factor B, refer to the results from Step 7 to characterize the evoked brain microstates across Factor B. That is, for the time period(s) that the ERP waveform did not differ as a function of Factor B, identify the microstate structure based on the results of Step 7 (i.e., Grand Mean, GmnB) and perform brain source localization on each of these microstate(s).
(10) For the time period(s) in which Step 8 shows significant differences in ERP waveform as a function of Factor B, refer to the results from Step 5 and Step 6 to characterize the distinct evoked brain microstates within each level of Factor B. That is, for the time period(s) that the ERP waveform did differ as a function of Factor B, identify the microstate structure separately for each level of Factor B (i.e., Step 5 and Step 6 above) and perform brain source localization on each of these microstate(s).

In the following example, Factor A is a between-subjects factor and Factor B is a within-subjects factor, so the simple main effect tests may be calculated within each level of A. The procedure may involve the following steps though the steps need not be performed sequentially unless a specific order is indicated based on a need for previous computations:

(1) Compute a difference snapshot between the a1b1 and a1b2 snapshots to create snapshots for the simple main effect for a1.
(2) Compute a difference snapshot between the a2b1 and a2b2 snapshots to create snapshots for the simple main effect for a2.
(3) Compute a difference snapshot between the simple main effects snapshots for a1 and for a2 to create the snapshots for the A×B interaction (i.e., the difference of the differences).
(4) Average the Mn_a1 and Mn_a2 snapshots to create a snapshot GmnB for a Grand Mean.
(5) Determine the stable and transition states for the simple main effect for a1.
(6) Determine the stable and transition states for the simple main effect for a2.
(7) Determine the stable and transition states for the simple main effects for a1 and a2. The output of this step specifies the periods of time during which Factors A and B interacted significantly (at an alpha-level determined by the confidence interval (CI) used—typically a 99% CI, producing an alpha-level of 0.01) to produce the observed brain microstates.
(8) Determine the stable and transition states for GmnB for the A×B interaction created in Step 4 to identify the periods of time in which Factors A and B did not interact to produce the brain microstates.
(9) For the epochs in which the results of Step 7 show no significant differences, refer to the results of Step 8 to characterize the evoked brain microstates. If main effects were also absent for this epoch, source localization may be performed on the observed microstate(s) during this epoch in the Grand Mean. If the main effect for Factor A and/or for Factor B is significant for this epoch, refer to the results above to characterize the evoked brain microstate(s) observed during this epoch.
(10) For the epochs in which the results of Step 7 show significant differences in the waveforms, refer to the results of Step 5 and Step 6 to characterize the distinct evoked brain microstates as a function of Factors A and B. For such an epoch, source localization may be performed on the observed microstate(s) during this epoch separately for the microstates identified and in Step 5 and in Step 6. Stable and transition states may be determined and source localization within each cell (e.g., a1b1, a1b2, a2b1, & a2b2) may also be performed as a means of breaking down the interaction to all possible pairwise comparisons.

Compared to existing methods (such as those based on k-clustering methods), the described micro-segmentation approach provides several advantages, including a data-driven (automatic) detection of non-periodic, quasi-stable states. Data-driven detection is achieved by using the baseline (period of time prior to the occurrence of an event) as a measure of an error variance to identify potential stable and discrete states that occur after the baseline. The method described herein provides a robust, reliable, and generalizable assessment for empirically deriving additional hypotheses.

The identification of the distinct, evoked brain microstates elicited by a stimulus makes it possible to investigate robust changes in the configuration of activation in electrical neuroimaging data, where a configuration of activation is defined as a topographical map—the average evoked potentials at a given recording bin across n-dimensional sensor space where n the number of EEG recording channels. The goal of the brain microstate approach is to provide information about the brain activity associated with the sequence of discrete information processing operations evoked by the presentation (or anticipation) of a stimulus within the context of a particular experimental task, with exogenous ERP components sensitive to the characteristics of the stimulus and endogenous ERP components sensitive to the stimulus in the context of the task. This sequence of information processing is composed of a series of stable brain activities, called brain microstates, each of which is characterized by the performance of specific cognitive computations and a relatively stable spatial distribution of brain activity.

The notion underlying the brain microstate approach is that each microstate refers to a time-limited information processing operation. Consistent with this notion, a growing body of studies shows that the presence of different brain microstates is associated with distinct cognitive operations. This approach suggests that the global pattern of brain electrical activity is modeled as being composed of a time sequence of decomposable brain microstates. Each brain microstate may remain significantly stable for a certain amount of time (e.g., for tens to hundreds of milliseconds), and then changes into another brain microstate that remains stable again. The notion of identifying stable brain microstates based on the spatiotemporal information represents an important insight into the understanding of the chronoarchitecture of brain processes, but the utility and adoption of this brain microstate approach were limited in part by constraints in the quantitative methods used by investigators to identify and interpret brain microstates.

Data analytic application 122 may include instructions to compute a difference waveform configuration between two n-dimensional ERPs by subtracting the ERP waveform elicited by one condition (e.g., ERP_A) from the ERP waveform elicited by another condition (ERP_B). The output of this difference waveform function is computed as ERP_A−ERP_B, which results in a T×n matrix with T as the number of timeframes and n as the number of electrodes. The difference waveform putatively represents physiological processes that are different between two conditions. The difference waveform function may be used as a first step towards the identification of differential stable microstates between two conditions that are better understood through the high performance microsegmentation of each condition, respectively.

A typical trial structure is: (i) jittered, variable-length baseline, (ii) stimulus onset, and (iii) post-stimulus period during which evoked microstates are identified and investigated. If the event-related anticipatory microstates are of interest, the trial structure could be modified as: (i) jittered, variable-length baseline, (ii) a fixed-interval pre-stimulus period that makes it possible for the subject to anticipate the stimulus onset (and during which evoked anticipatory microstates can be identified and investigated), (iii) stimulus onset, and (iv) post-stimulus period (during which evoked microstates can be identified and investigated).

Figure 19:
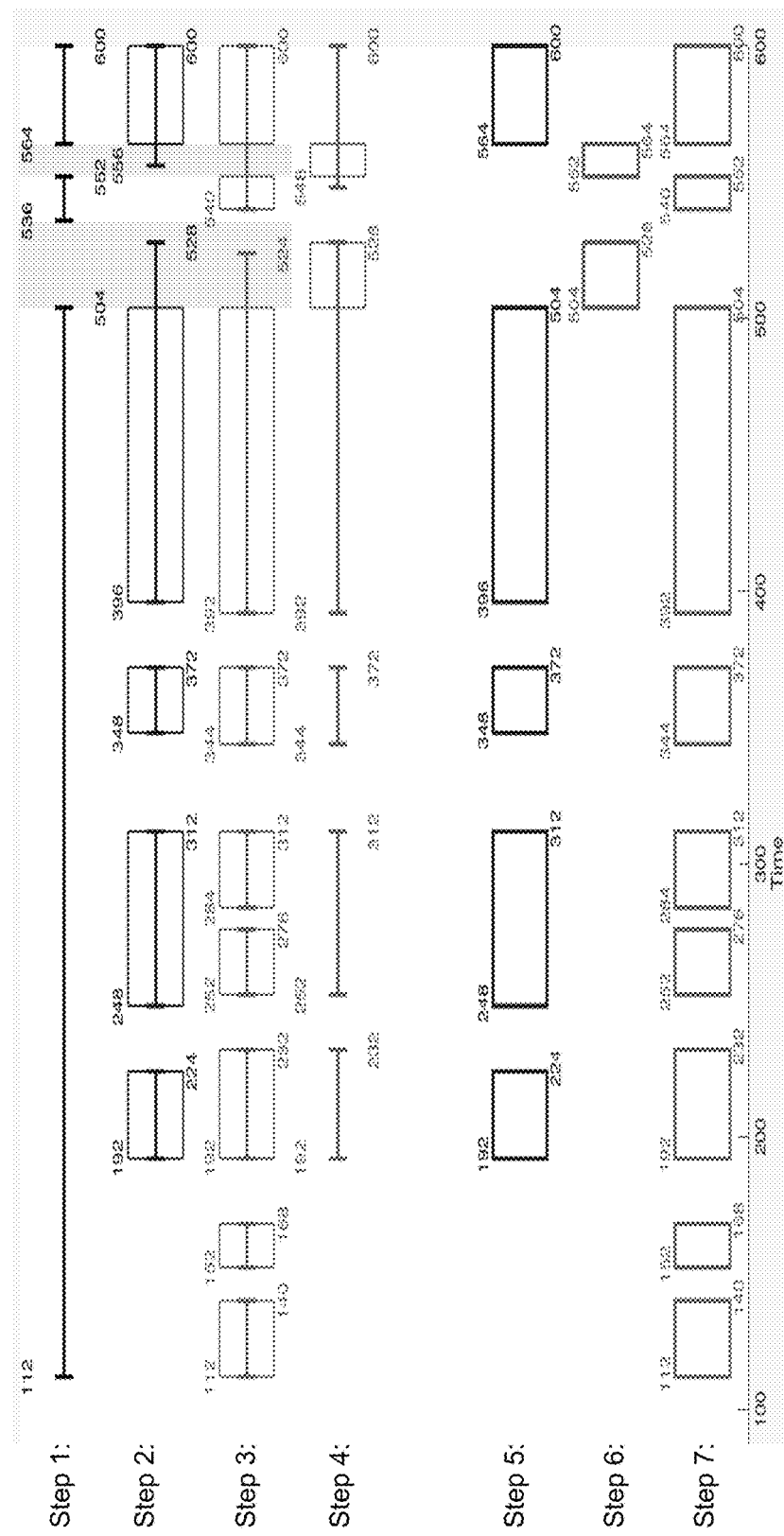
FIG. 19 shows sample output at seven steps in accordance with an illustrative embodiment.

A script may allow users to perform various steps with a single button click. In the case of an experimental design with two conditions (CONDITION I and CONDITION II), the script allows users to perform eight steps at once with sample output for steps 1-7 shown in FIG. 19 in accordance with an illustrative embodiment:

1) Perform a difference wave function;
2) Perform a high-performance microsegmentation suite CONDITION 1;
3) Perform a high-performance microsegmentation suite of CONDITION 2;
4) Perform a high-performance microsegmentation suite of the grand mean
5) Output the brain microstates specific to CONDITION 1;
6) Output the brain microstates common to both CONDITION 1 & CONDITION 2;
7) Output the brain microstates specific to CONDITION 2; and
8) Create template map files including results from steps 5-7.

The processing supported by data analytic application 122 as described herein may be distributed between one or more analytic tools. For example, a first analytic tool may use the RMSE to identify stable states and transition states across discrete event-related brain microstates. A second analytic tool may use the similarity metric based on cosine distance in n dimensional sensor space to determine whether template maps for successive brain microstates differ in configuration of brain activity. A third analytic tool may use GFP metrics to identify changes in the overall level of activation of the brain. The one or more analytic tools may be integrated.

The RMSE analysis performed by data analytic application 122 may identify significant changes in the stable event-related pattern of EEG activation across the n-dimensional sensor space. However, there are two reasons such a change in the RMSE function may occur: (1) a different stable event-related microstate was elicited, typically interpreted as meaning that one or more of the cortical sources underlying the prior event-related microstate had changed; or (2) the same stable event-related microstate was maintained, but GFP increased (or decreased), typically interpreted as meaning that the level of activation of the set of cortical sources underlying the event-related microstate had increased (or decreased). Once the putative stable microstates have been identified using the RMSE, each topographical map within a microstate can be expressed within a n-dimensional (e.g., 128-dimensional) vector space, the mean template map for the microstate can be expressed in this microstate, and a confidence interval region can be determined around this template map in 128-dimensional space. If the succeeding event-related microstate identified by RMSE is the result of a change in the location of the underlying neural sources of the n-dimensional event-related waveform, the cosine metric between the template map for an event-related microstate and the template map for the succeeding microstate should differ. This is because different configurations of activity produce different vector angles in n-dimensional vector space. However, if the succeeding event-related microstate identified by RMSE is the result of a change in the level of neural activation (i.e., GFP) rather than a change in source location, then the representation of these microstates in n-dimensional vector space differ in the length of the vector, but not in the angle of the vector.

A comparison of these outputs permits identification of which microstates identified by the RMSE analysis are determined by the analysis based on the cosine metric as the same microstate, but at a different GFP. Changes in GFP levels within the same microstate are provided in the GFP outputs for the microstates in the preliminary results that were merged in the final results.

By analyzing time-varying activity in a multi-dimensional sensor space (across the entire scalp) rather than in a single vector space (at specific electrode positions), data analytic application 122 makes it possible to investigate possible neural organizations underlying baseline states even in the absence of a clear morphological peak or trough. Because the results differentiate stable brain microstates from transitions between states, data analytic application 122 provides a better basis for source localization algorithms used to investigate the underlying neural correlates for these microstates. This, in turn, may lead to the identification of more defined biomarkers for various neuropsychiatric and neurologic diseases.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more". Still further, using "and" or "or" in the detailed description is intended to include "and/or" unless specifically indicated otherwise. The illustrative embodiments may be implemented as a method, apparatus, or article of manufacture using standard programming and/or engineering techniques to produce software, firmware, hardware, or any combination thereof to control a computer to implement the disclosed embodiments.

The foregoing description of illustrative embodiments of the disclosed subject matter has been presented for purposes of illustration and of description. It is not intended to be exhaustive or to limit the disclosed subject matter to the precise form disclosed, and modifications and variations are possible in light of the above teachings or may be acquired from practice of the disclosed subject matter. The embodiments were chosen and described in order to explain the principles of the disclosed subject matter and as practical applications of the disclosed subject matter to enable one skilled in the art to utilize the disclosed subject matter in various embodiments and with various modifications as suited to the particular use contemplated.

What is claimed is:

1. A non-transitory computer-readable medium having stored thereon computer-readable instructions that when executed by a computing device cause the computing device to:
receive data, wherein the data includes a plurality of snapshots, wherein each snapshot of the plurality of snapshots includes a plurality of sensor measurements captured from distinct sensors at a common time, wherein the plurality of snapshots are time ordered and associated with a subject;
compute first root mean square error (RMSE) values between successive pairs of the plurality of snapshots in time order that occur during a predefined baseline interval;
compute a mean value of the computed first RMSE values;
compute a standard deviation value of the computed first RMSE values using the computed mean value;
compute a confidence interval parameter value using the computed standard deviation value and a predefined state confidence parameter value;
compute second RMSE values between successive pairs of the plurality of snapshots in time order that occur after the predefined baseline interval;
identify a peak in the computed second RMSE values based on a first comparison with the computed confidence interval parameter value;
identify a valley in the computed second RMSE values based on a second comparison with the computed confidence interval parameter value;
determine a stable state as occurring from the identified peak to the identified valley; and
output a start time and a stop time for the determined stable state for the subject based on the start time being associated with the identified peak and on the stop time being associated with the identified valley.

2. The non-transitory computer-readable medium of claim 1, wherein the successive pairs of the plurality of snapshots in time order are separated by a pre-defined lag value.

3. The non-transitory computer-readable medium of claim 1, wherein a plurality of peaks are identified in the computed second RMSE values and a plurality of valleys are identified in the computed second RMSE values, wherein the peak is included in the plurality of peaks and the valley is included in the plurality of valleys.

4. The non-transitory computer-readable medium of claim 3, wherein a plurality of stable states are determined, wherein the determined stable state is included in the plurality of stable states, wherein each stable state is determined as occurring from a peak of the plurality of peaks to a subsequent valley of the plurality of valleys.

5. The non-transitory computer-readable medium of claim 4, wherein a plurality of transition states are determined, wherein each transition state is determined as occurring from a valley of the plurality of valleys to a subsequent peak of the plurality of peaks.

6. The non-transitory computer-readable medium of claim 4, wherein each stable state is determined as occurring from the peak of the plurality of peaks to the subsequent valley of the plurality of valleys, inclusive.

7. The non-transitory computer-readable medium of claim 4, wherein the computer-readable instructions further cause the computing device to:
compute a mean template map for each stable state of the plurality of stable states, wherein the mean template map includes the sensor measurements captured from distinct sensors averaged across the snapshots that occur between the peak and the subsequent valley of a respective stable state;
compute a standard deviation for each stable state of the plurality of stable states using the computed mean template map and the sensor measurements captured from distinct sensors for the snapshots that occur between the peak and the subsequent valley for the respective stable state;
compute a confidence value for each stable state of the plurality of stable states using the computed standard deviation for the respective stable state and a similarity metric confidence value;
compute a similarity value between successive stable states of the plurality of stable states; and
indicate the successive stable states are similar when the computed similarity value is less than the computed confidence value for a stable state of the successive stable states.

8. The non-transitory computer-readable medium of claim 7, wherein the similarity value is computed using $$Sim(A, B) = 1 - \frac{A \cdot B}{\|A\|\|B\|},$$

where A is a first stable state of the successive stable states and B is a second stable state of the successive stable states.

9. The non-transitory computer-readable medium of claim 1, wherein each RMSE value of the first RMSE values and the second RMSE values is computed using $$RMSE = \sqrt{\frac{\sum_{i=1}^{n}(x_i - \hat{x}_i)^2}{n}},$$

where n is a number of the distinct sensors, $x_i$ is a sensor measurement value at sensor i in a current snapshot, and $\hat{x}_i$ is a sensor measurement value at sensor i in a previous snapshot.

10. The non-transitory computer-readable medium of claim 9, wherein the current snapshot and the previous snapshot are separated in time by a pre-defined lag value.

11. The non-transitory computer-readable medium of claim 1, wherein the peak is identified in the computed second RMSE values after removing local maxima that represent noise.

12. The non-transitory computer-readable medium of claim 1, wherein the valley is identified in the computed second RMSE values after removing local minima that represent noise.

13. The non-transitory computer-readable medium of claim 1, wherein identifying the peak comprises computer-readable instructions that further cause the computing device to:
identify a local maxima in the computed second RMSE values;
define a previous valley value; and
when a value of the identified local maxima is greater than the defined previous valley value plus the computed confidence interval parameter value and the value of the identified local maxima minus a subsequent RMSE value is greater than the computed confidence interval parameter value, the identified local maxima is the identified peak.

14. The non-transitory computer-readable medium of claim 13, wherein the previous valley value is initialized to the computed mean value.

15. The non-transitory computer-readable medium of claim 13, wherein identifying the valley comprises computer-readable instructions that further cause the computing device to:
identify a local minima in the computed RMSE values;
define a previous peak value; and
when the defined previous peak value minus a value of the identified local minima is greater than the computed confidence interval parameter value and a subsequent RMSE value minus the value of the identified local minima is greater than the computed confidence interval parameter value, the identified local minima is the identified valley.

16. The non-transitory computer-readable medium of claim 15, wherein the previous peak value is initialized to the computed mean value.

17. The non-transitory computer-readable medium of claim 15, wherein the defined previous peak value is a value of the identified peak.

18. The non-transitory computer-readable medium of claim 15, wherein the previous valley value is redefined as a value of the identified valley.

19. A computing device comprising:
a processor; and
a non-transitory computer-readable medium operably coupled to the processor, the computer-readable medium having computer-readable instructions stored thereon that, when executed by the processor, cause the computing device to
receive data, wherein the data includes a plurality of snapshots, wherein each snapshot of the plurality of snapshots includes a plurality of sensor measurements captured from distinct sensors at a common time, wherein the plurality of snapshots are time ordered and associated with a subject;
compute first root mean square error (RMSE) values between successive pairs of the plurality of snapshots in time order that occur during a predefined baseline interval;
compute a mean value of the computed first RMSE values;
compute a standard deviation value of the computed first RMSE values using the computed mean value;
compute a confidence interval parameter value using the computed standard deviation value and a predefined state confidence parameter value;
compute second RMSE values between successive pairs of the plurality of snapshots in time order that occur after the predefined baseline interval;
identify a peak in the computed second RMSE values based on a first comparison with the computed confidence interval parameter value;
identify a valley in the computed second RMSE values based on a second comparison with the computed confidence interval parameter value;
determine a stable state as occurring from the identified peak to the identified valley; and
output a start time and a stop time for the determined stable state for the subject based on the start time being associated with the identified peak and on the stop time being associated with the identified valley.

20. A method of identifying states in a time ordered sequence of data that have a temporal component, the method comprising:
receiving data, wherein the data includes a plurality of snapshots, wherein each snapshot of the plurality of snapshots includes a plurality of sensor measurements captured from distinct sensors at a common time, wherein the plurality of snapshots are time ordered and associated with a subject;
computing, by a computing device, first root mean square error (RMSE) values between successive pairs of the plurality of snapshots in time order that occur during a predefined baseline interval;
computing, by the computing device, a mean value of the computed first RMSE values;
computing, by the computing device, a standard deviation value of the computed first RMSE values using the computed mean value;
computing, by the computing device, a confidence interval parameter value using the computed standard deviation value and a predefined state confidence parameter value;
computing, by the computing device, second RMSE values between successive pairs of the plurality of snapshots in time order that occur after the predefined baseline interval;
identifying, by the computing device, a peak in the computed second RMSE values based on a first comparison with the computed confidence interval parameter value;
identifying, by the computing device, a valley in the computed second RMSE values based on a second comparison with the computed confidence interval parameter value;
determining, by the computing device, a stable state as occurring from the identified peak to the identified valley; and
outputting, by the computing device, a start time and a stop time for the determined stable state for the subject based on the start time being associated with the identified peak and on the stop time being associated with the identified valley.

* * * * *